(12) United States Patent
Acharya et al.

(10) Patent No.: US 7,501,499 B2
(45) Date of Patent: Mar. 10, 2009

(54) MODIFIED HEMOGLOBIN AND METHODS OF MAKING SAME

(75) Inventors: Seetharama A. Acharya, Cresskill, NJ (US); Belur N. Manjula, Cresskill, NJ (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 147 days.

(21) Appl. No.: 10/538,976

(22) PCT Filed: Dec. 18, 2003

(86) PCT No.: PCT/US03/40407

§ 371 (c)(1),
(2), (4) Date: Dec. 5, 2005

(87) PCT Pub. No.: WO2004/058291

PCT Pub. Date: Jul. 15, 2004

(65) Prior Publication Data

US 2006/0135753 A1 Jun. 22, 2006

Related U.S. Application Data

(60) Provisional application No. 60/436,149, filed on Dec. 23, 2002.

(51) Int. Cl.
*G01N 33/72* (2006.01)
*C08H 1/00* (2006.01)
*A61K 38/00* (2006.01)

(52) U.S. Cl. ............... 530/402; 507/136; 436/15

(58) Field of Classification Search ............... None
See application file for complete search history.

(56) References Cited

U.S. PATENT DOCUMENTS

| | | | |
|---|---|---|---|
| 5,234,903 A * | 8/1993 | Nho et al. ............ 514/6 |
| 5,585,484 A | 12/1996 | Acharya et al. |
| 5,750,725 A | 5/1998 | Acharya et al. |
| 6,017,943 A * | 1/2000 | Acharya et al. ............ 514/410 |
| 6,773,613 B1 | 8/2004 | Winslow et al. |
| 6,844,317 B2 | 1/2005 | Winslow et al. |
| 6,974,795 B2 * | 12/2005 | Winslow et al. ............ 514/6 |
| 7,019,117 B2 | 3/2006 | Acharya et al. |
| 7,144,989 B2 * | 12/2006 | Acharya et al. ............ 530/385 |
| 7,169,900 B2 | 1/2007 | Acharya et al. |
| 7,271,145 B2 | 9/2007 | Winslow et al. |
| 2004/0002443 A1 | 1/2004 | Acharya et al. |
| 2005/0159339 A1 | 7/2005 | Acharya et al. |
| 2005/0201988 A1 | 9/2005 | Acharya et al. |
| 2006/0111275 A1 | 5/2006 | Acharya et al. |

FOREIGN PATENT DOCUMENTS

WO WO 03/008932 A2 1/2003
WO WO 2007/050121 A2 5/2007

OTHER PUBLICATIONS

Wikipedia (2007, updated) "Hemoglobulin", http://en.wikipedia.org/wiki /Hemoglobin, pp. 1-2.*
Wikipedia (2008, updated) Polyethylene glycol, "en.wikipedia.org/wiki/Polyethylene_glycol", pp. 1-4.*
Juszczak et al., "UV Resonance Raman Study of β93-Modified Hemoglobin A: Chemical Modifier-Specific Effects and Added Influences of Attached Poly(ethylene glycol) Chains," Biochemistry 41:376-385 (Jan. 2002).
Manjula et al., "Site-Specific PEGylation of Hemoglobin at Cys-93(β): Correlation Between the Colligative Properties of the PEGylated Protein and the Length of the Conjugated PEG Chain." Bioconjugate Chem. 14:464-472 (2003).
Manjula et al., "Cys-99-ββ-Succinimidophenyl Polyethylene Glycol 200 Hemoglobin A." The Journal of Biological Chemistry 275, 8:5527-5534 (Feb. 2000).
Vandegriff et al., "MP4, A New Nonvasoactive PEG-Hb Conjugate." Transfusion 43:509-516 (Apr. 2003).
Shorr R G et al., entitled "Changes in the Functional Properties of Bovine Hemoglobin Induced by Covalent Modification with Polyethylene Glycol," Art. Cells, Blood Subs. and Immob. Biotech., 27(3), 185-202 (1999).
Goverment of India Patent Office Examination Letter dated Oct. 17, 2007 in connection with related Indian Patent Application Serial No. 2820/DELNP/2005.
Supplementary European Search Report for European Patent Application No. EP 03 799982.8 dated Oct. 24, 2007.

* cited by examiner

*Primary Examiner*—Jon P Weber
*Assistant Examiner*—Samuel W Liu
(74) *Attorney, Agent, or Firm*—Amster, Rothstein & Ebenstein LLP

(57) ABSTRACT

The present invention provides a hemoglobin molecule (Hb) having six ± one PEG chains, wherein two of said PEG chains are bound to Cys-93 (β) of Hb, and the remaining PEG chains are bound to thiol groups introduced on $\epsilon$-$NH_2$ of Hb. The present invention also provides a process for preparing a modified hemoglobin molecule (Hb), comprising the steps of: (a) reacting Hb with 8-15 fold excess of iminothiolane to form thiolated Hb; and (b) reacting the thiolated Hb with 16-30 fold excess of PEG functionalized with a maleimide moiety, to form the modified Hb.

14 Claims, 10 Drawing Sheets

A

B

Iminothiolane      γ-Mercaptobutyrimidyl-Hb

Amidination of amino group of Hb with Iminothiolane

300-MHz $^1$H-NMR spectra of 3% solutions of Hb A, P5K6-HbA, P20K2-HbA'
in the CO form [(A) and (B)] and in the deoxy form [(C) and (D)] in $H_2O$ in 0.1 M
phosphate buffer in the presence of 5% $D_2O$ at pH7.0 and 29 °C.

A. Exchangeable Proton Resonances

B. Ring-Current-Shifted Proton Resonances

C. Hyperfine-Shifted N$_δ$H Resonances of Proximal Histidines

D. Hyerfine-Shifted and Exchangeable Proton Resonances.

MODIFIED HEMOGLOBIN AND METHODS OF MAKING SAME

CROSS-REFERENCE TO RELATED APPLICATIONS

This application is a U.S. national stage entry under 35 U.S.C. §371 of PCT International Patent Application No. PCT/US2003/040407, filed on Dec. 18, 2003, and claims priority to U.S. Provisional Patent Application No. 60/436,149, filed on Dec. 23, 2002.

STATEMENT OF GOVERNMENT SUPPORT

The invention disclosed herein was made with U.S. Government support under grant number HL71064 from the National Institutes of Health and grant number PR023085 from the U.S. Army. Accordingly, the U.S. Government has certain rights in this invention.

FIELD OF INVENTION

The present invention relates to a modified hemoglobin and methods of making the same.

BACKGROUND OF THE INVENTION

Hemoglobin (Hb) is the major constituent of the erythrocyte which carries oxygen from the lungs throughout the body. When contained in red blood cells, Hb exists as a tetramer structure composed of two oxygen linked $\alpha\beta$ dimers each having a molecular weight of about 32 Kd. Each $\alpha$ and $\beta$ subunit of each dimer has a protein chain and a heme molecule. The sequences of the $\alpha$ and $\beta$ protein chains are known. Hb is a potentially useful blood substitute for transfusions, and has been proposed as a reagent to trap nitric oxide in septic shocks, and to modulate tissue oxygenation during the radiation therapy of cancer. Recombinant DNA technology also has afforded the generation of modified Hb with oxygen affinities modulated for special needs of individual therapeutic applications.

Vasoactivity of acellular Hb, i.e. the constriction of arterioles and capillaries, when infused with purified acellular Hb solutions, or intra molecularly crosslinked Hbs, has been the major impediment for developing Hb-based oxygen carriers (Savitzsky et al. 1978, Sloan et al. 1999, Saxena et al. 1999). The vasoactivity has been attributed to the NO scavenging effect of Hb (Doharty et al. 1998). Two molecular approaches, that are very distinct from one another, have been advanced to in an attempt to overcome NO scavenging activity of Hb. The first approach is the recombinant DNA approach, which has attempted to reduce the nitric oxide scavenging activity of Hb by modifying the NO binding activity of Hb by site-specific mutagenesis of the distal heme pocket (Eich et al, 1996). The second approach is the chemical approach, in which the molecular size of Hb is enhanced through oligomerization, which will reduce or possibly completely inhibit the extravasation of Hb from the vascular space into the interstitial space (Hess et al. 1978, Thomas et al. 1993, Muldoon et al. 1996, Macdonal et al. 1994, Furchgott 1984, Kilbourn et al. 1994). However, the size-enhancing approach will be successful only if the vasoactivity of Hb is essentially mediated as a result of extravasation. Though the oligomerization mediated size enhancement of Hb has shown some reduction in the vasoactivity of Hb, a non-hypertensive Hb solution has not been generated by either recombinant DNA technology or by the size enhancement approach that involved the oligomerization of Hb using small molecular bifunctional reagent. One exception is the oligomerized product of Hb (Matheson et al. 2002), that has a molecular size far in excess of 300 kDa and with an average molecular radius of 24 nm, and was found to be non-hypertensive and found not to extravasate. However, most of the current oligomerized products that are in clinical trials have a molecular weight in the range of 200 to 250 kDa.

The demonstration that Enzon polyethylene glycolylated (PEGylated) Hb, that carries ten copies of PEG-5000 chains linked to Hb at its $\alpha$ and $\epsilon$-amino groups is non-hypertensive has stimulated the research in the blood substitute field (Rolfs et al. 1998). The NO binding activity of intra-tetramerically crosslinked Hbs, oligomerized Hbs and PEGylated Hbs (Winslow et al, 1998, Vandegriff et al, 1997) do not show a direct correlation with their 'pressor effects'. Thus, the reduction in the 'pressor activity' of acellular Hb does not appear to be a direct correlate of, either the NO binding activity of the preparation or of the molecular size of the preparation. But the PEGylated Hbs exhibited considerably lower level of vasoactivity as compared to the oligomerized Hb. The PEG-Bv-Hb of Enzon that carries 10 copies of PEG-5,000 exhibited hardly any 'pressor effect'. Vandegriff et al (1998) have noted that PEG-Bv-Hb exhibited high viscosity and oncotic pressure as compared to that of oligomerized samples of Hb. The molecular radius of Enzon PEGylated Bv-Hb calculated from the oncotic pressure was considerably larger (15 nm) than that of oligomerized Hbs and the molecular radius calculated is not consistent with its calculated molecular mass of 114,000 daltons (Vandegriff et. al. 1998). Accordingly, it has been hypothesized that size of Hb should be increased to a molecular radius of around 15 nm, and this should be accompanied by considerable increase in the viscosity and oncotic pressure to generate a non-hypertensive Hb solution (Winslow 1999).

In the non-hypertensive Enzon Pegylated Hb, PEG-5000 chains are linked to the $\alpha$ and $\epsilon$-amino groups of bovine Hb PEG-chains by isopeptide bonds. The covalent attachment of PEG is accompanied by the loss of the net positive charge of the amino groups derivatized. In a recent study, it was demonstrated that monofunctional modification of rHb1.1 with glutaraldehyde, lowers the vasoactivity of Hb to some degree, though the oligomerization of rHb1.1 reduces the vasoactivity of Hb to a higher degree. Thus in understanding the molecular basis of neutralization of the vasoactivity of Hb by PEGylaltion, the potential role of the modification of the surface charge of Hb that accompanies the PEGylation of HB needs to be considered.

To expose the correlation between the perturbation of the surface charge of Hb resulting from PEGyaltion with the generation of non-hypertensive Hb, new approaches have been developed relating to the conservation PEGylation of Hb, i.e. PEG-modification of Hb without altering the surface charge of Hb (Acharya et al. 1996). The high reactivity and selectivity of PEG-maleimide to Cys-93($\beta$) of Hb under oxy conditions has been used to prepare homogeneous PEGylated Hb carrying two copies PEG-chains per tetramer. Three different preparations of PEG-HbA carrying two copies each of PEG-5K, or PEG-10K or PEG-20K have been generated. The changes in the molecular volume (hydrodynamic volume), molecular radius, viscosity, and oncotic pressure of Hb has been correlated with the mass of the PEG covalently linked to Hb; and all of these molecular properties have been correlated with pressor effect. Though the viscosity and the oncotic pressure of $(PEG_{20K})_2$-Hb is comparable to that of Enzon PEG-Bv-Hb, a non-hypertensive Hb molecule, this PEGylated Hb was vasoactive. Thus, the solution to vasoactivity problem cannot be achieved by simply endowing the molecule with an increase in viscosity, oncotic pressure and the molecular volume (hydrodynamic volume).

SUMMARY OF THE INVENTION

The present invention provides a modified Hb that has enhanced molecular volume, high viscosity, high oncotic pressure, high $O_2$ affinity, is non-hypertensive and also solves the vasoactivity problem. Additionally, the modified Hb of the present invention can be manufactured in a simple, flexible and highly efficient process, that makes the production of the modified Hb of the present invention cost-efficient.

More particularly, the present invention provides a hemoglobin molecule (Hb) having six±one PEG chains, wherein two of said PEG chains are bound to Cys-93($\beta$) of Hb, and the remaining PEG chains are bound to thiol groups introduced on $\epsilon$-$NH_2$ of Hb.

The present invention also provides a process for preparing a modified hemoglobin molecule (Hb), comprising the steps of: (a) reacting Hb with 8-15 fold excess of iminothiolane to form thiolated Hb; and (b) reacting the thiolated Hb with 16-30 fold excess of PEG functionalized with a maleimide moiety, to form the modified Hb.

Finally, the present invention provides a modified Hb molecule prepared in accordance with the foregoing process.

DETAILED DESCRIPTION OF THE INVENTION

As used herein, and unless noted otherwise, "Hb" includes hemoglobin from human and mammalian sources (e.g., bovine Hb, swine Hb), recombinant Hb, as well as Hb (isolated or recombinant Hb) that has been modified to increase or decrease oxygen affinity and/or autooxidation. Additionally, Hb may include intramolecularly crossbridged Hb (isolated or recombinant Hb), including for example, Hb that has been cross-linked at Cys-93($\beta$) using bis maleidophenyl PEG (MW of PEG chain of the bifunctional reagent is 2000 to 10,000 daltons), $\alpha\alpha$-fumaryl Hb, or $\beta\beta$-fumaryl Hb or $\beta\beta$ subaryl HbA.

In the present invention, the Hb has or is carrying six±one PEG chains, wherein two of the PEG chains are bound to Cys-93(β) of Hb, and the remaining PEG chains are bound to thiol groups introduced on ε-$NH_2$ of Hb. The thiol groups are preferably associated with γ-mercapto butyramidinated ε-$NH_2$ of Hb. In the preferred embodiment, each PEG chain has a molecular weight of 3000-10,000 daltons, and more preferably has a molecular weight of about 5000 daltons. The PEG chains are also preferably linked to Hb by a succinmidyl linkage. In the preferred embodiment, the Hb molecules of the present invention are also non-hypertensive.

The Hb molecule of the present invention is prepared by reacting Hb with 8-15 fold excess of iminothiolane to form thiolated Hb; and then reacting the thiolated Hb with 16-30 fold excess of PEG functionalized with a maleimide moiety, to form the modified Hb. In the preferred embodiment, Hb is reacted with 9-12 fold excess iminothiolane in step (a) and the thiolated Hb is preferrably reacted with 18-22 fold excess PEG functionalized with a maleimide moiety. In the more preferred embodiment, Hb is reacted with about 10 fold excess iminothiolane in step (a), and the thiolated Hb is reacted with about 20 fold excess PEG functionalized with a maleimide moiety in step (b). It is also within the confines of the present invention that the thiolation of Hb and the PEG-modification of the thiolated Hb can be carried out either simultaneously, or in a two step process. With respect to the molecular weight of PEG used in the process, the PEG preferably has a molecular weight of 3000-10,000 daltons, and more preferably has a molecular weight of about 5,000 daltons. In the most preferred embodiment, the modified Hb resulting from the process is non-hypertensive.

In the process of the invention, the modified Hb may be prepared directly from mammalian Hb carrying multiple oxy confirmation specific reactive thiol groups (dog Hb, cat Hb, chicken Hb, mouse Hb) or recombinant human Hb with additional reactive cysteines at the desired positions on the α and β-chains, which is treated with the excess PEG functionalized with a maleimide moiety to arrive at the modified Hb.

Figure 1:
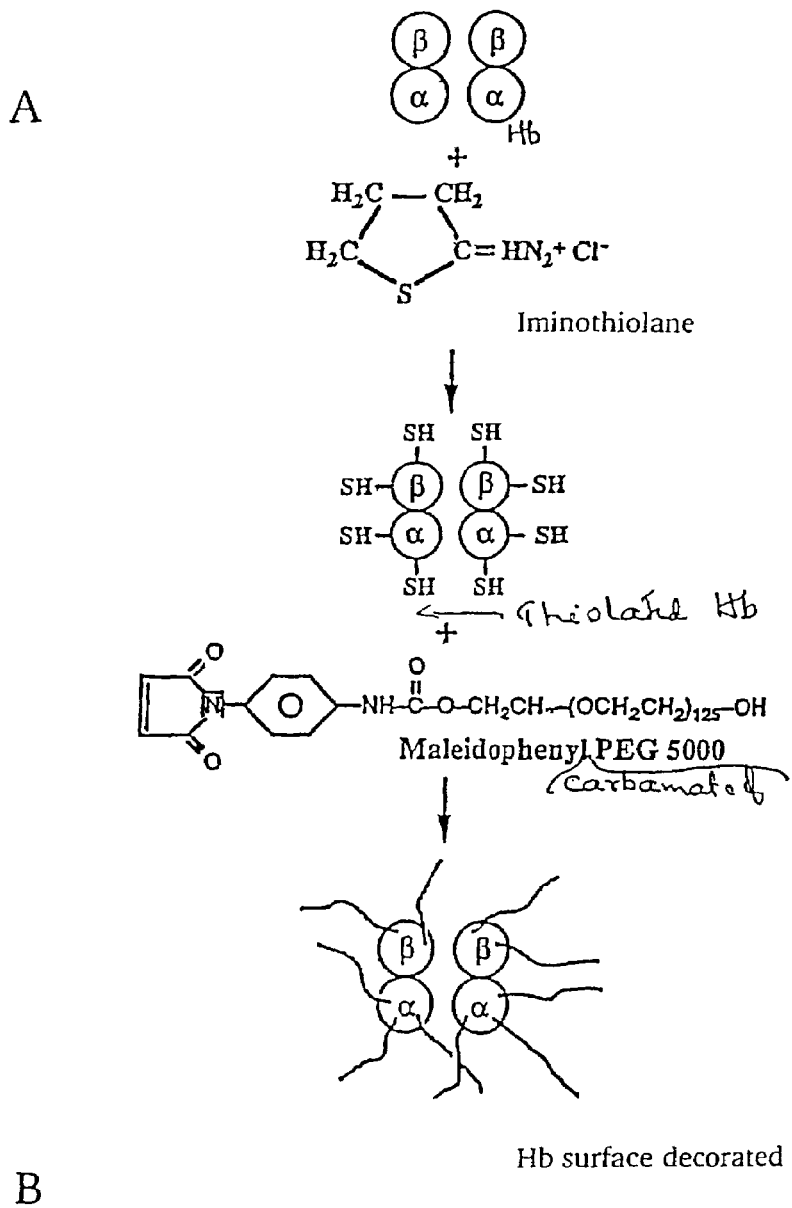
FIG. 1 provides a schematic representation of the iminothiolane dependent thiolation mediated maleimide chemistry based PEGylation of Hb. A: depicts the thiolation, the first phase of the PEGylation reaction in a simplified fashion and the conjugation of the PEG-chains functionalized as maleimided to the thiolated protein. The PEG-chains linked are depicted as arms projecting out of the central protein (Hb) core. B: The reaction of iminothiolane with the $\epsilon$-amino groups of Hb generating $\gamma$-mercapto butyramidinyl moieties.
Figure 1:
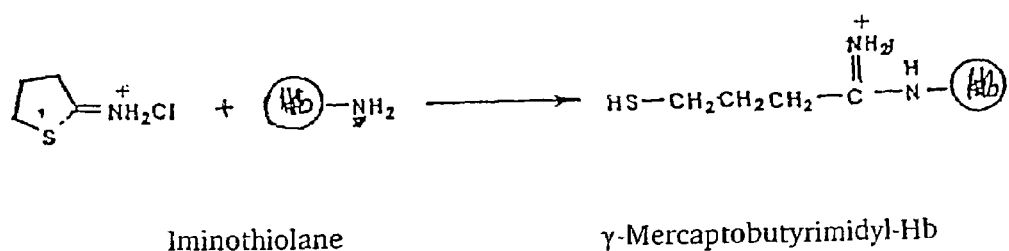

The chemistry surrounding the process is schematically presented in FIGS. 1A and 1B. Iminothiolane, does not carry free thiol groups, and the thiol group is generated in situ once it reacts with the ε-amino groups. The derivatized ε-amino group (an amidine) retains the original positive charge of this functional group (FIG. 1B). Therefore, Hb can be incubated with PEG-maleimide together with the thiolating reagent to generate PEGylated Hb, without the danger of the thiolating reagent consuming the PEG-maleimide reagent. The level of PEGylation is determined by the level of thiolation (reaction of iminothiolane with Hb). The latter is primarily a function of the concentration of iminothiolane and the reactivity of the ε-amino groups of Hb in a given conformational state towards amidination by iminothiolane.

The PEGylation reaction is flexible in that the reaction is independent of both the molecular size of PEG in the maleimide and the linker chemistry between the maliemide and PEG-chain in the PEG-maleimide. The approach can be used to enhance the molecular volume (size) of Hb to any desired level by modulating the level of thiolation of Hb and/or the molecular mass of PEG in the PEG-maleimide. The conservative PEGylation Technology has been optimized to generate multiple, size-enhanced PEGylated Hbs with high oxygen affinity. The modified Hb of the present invention exhibits a high degree of molecular homogeneity both in terms the net charge and the hydrodynamic volume, the hydrodynamic volume corresponding to that of a globular protein of a molecular weight of ~250,000 daltons. It is believed that any design of a non-hypertensive PEGylated Hb should attempt to shield a larger molecular surface of Hb by using a larger number of PEG-chains of smaller mass.

The present invention may be better understood by reference to the following non-limiting Example. The following Example is presented in order to more fully illustrate the preferred embodiments of the invention, and should in no way be construed as limiting the scope of the present invention.

EXAMPLE 1

I. Materials and Methods

Hemoglobin. Human HbA was purified from the erythrocyte lysate as described earlier (Acharya et al. 1983).

Synthesis of Maleidophenyl Polyethylene Glycol (Mal-PhePEG) reagents. Mono functional maleidophenyl derivatives of PEG5000 and PEG10000 were synthesized according to the procedures of Acharya, et al. 1996. Maleidoethyl PEG-5000 was purchased by Shaerwaters, Huntsville, Ala.

Reaction of HbA with the MalPhe-PEG reagents. Hemoglobin A (0.5 mM) in PBS, pH 7.4 was reacted with a 10 fold molar excess of Mal Phe PEG-5000 at 4° C. Modification of HbA by PEG was monitored by reverse phase high-pressure liquid chromatography (RPHPLC) and size exclusion chromatography (SEC). The reaction product was dialyzed against 50 mM Tris-acetate buffer, pH 8.5 and subjected to purification by ion exchange chromatography. The PEGylated Hbs were purified by ion exchange chromatography on Amersham Biosciences Q-Sepharose High Performance resin, using an AKTA Explorer 10 Protein Purification System. The Q-Sepharose High Performance column (2.6 cm×62 cm) was equilibrated with 50 mM Tris-acetate buffer, pH 8.5, and the protein was eluted with a linear decreasing pH gradient consisting of 50 mM Tris-acetate, pH 8.5 and 50 mM Tris-acetate, pH 7.0 over 8 column volumes. The column effluent was monitored at 240 and 540 nm.

Oxygen affinity measurements. Oxygen equilibrium curves were measured at 37° C. using a Hem-O-Scan (Aminco) in PBS, pH 7.4 at a hemoglobin tetramer concentration of 1 mM.

Viscosity measurements. The viscosity of the PEGylated Hbs was measured in a Rheometer, at a protein concentration of 4 g/dl, in PBS buffer, pH 7.4 and at 37° C. The instrument was calibrated with deionized water prior to measurements of the viscosity of the Hb samples.

Colloidal osmotic pressure measurements. The colloidal osmotic pressure of the PEGylated hemoglobins was determined using a Wescor 4420 Colloidal Osmometer. All measurements were done using 2 g/dl hemoglobin samples in PBS, pH 7.4 at room temperature. A 30 kDa cut-off membrane was used. The instrument was tested with Osmocoll references standards prior to measurements of the samples.

RPHPLC analysis of PEGylated Hbs. The globin chains of the various PEGylated Hbs were analyzed by RPHPLC, by methods previously described. Briefly, the separation was carried out on a Vydac C4 (4.6×250 mm) column, employing a linear gradient of 35-50% acetonitirile containing 0.1% TFA in 100 min. The column effluent was monitored at 210 nm.

Vasoactivity of PEGylated Hbs. Investigations were carried out in a hamster skin fold window microcirculation model, essentially according to the procedures previously described (Mirhashemi et al. 1988, Tsai et al. 1996). Studies were performed on male Golden Syrian Hamsters (Charles Rivers, U.S.A.) of 55-70 g body weight. All animal studies were approved by the Animal Subject Committee of University of California, San Diego, and performed according to NIH guidelines for the care and use of laboratory animals (NIH publication #85-23 Rev. 1985).

Each animal served as its own baseline. A 10% hypervolemic infusion was made at a rate of 0.20 ml/min into the animal via the jugular vein catheter using a microinfusion pump (CMA 100 Microinjection Pump: CMA, Sweden). The blood pressure, the arteriolar diameter and functional capillary density were measured immediately following the infusion and 30 min after the infusion.

Kinetics of thiolation of Hb by iminothiolane. The amidination of Hb by iminothiolane could be followed by estimating the extent of thiolation. The number of thiol groups in a sample of Hb incubated with an amount of iminothiolane for a given length of time is estimated using dithiopyridine as described by Ampuslki (1969). A stock solution of 4,4'dithiopyridines (4-PDS, MW=220.32, Aldrich Chemical Co.) was prepared by dissolving the reagent in PBS to a final concentration of 3 mM (or higher if desired). An aliquot of Hb incubated with iminothiolane was incubated with dithiopyridine and the number reactive sulfhydryl groups on the protein is estimated by the conversion of 4-PDS to 4-thiopyridone (4-TP) that can be monitored at monitored at 324 nm ($\epsilon_{324}$=1.98×10$^{-4}$ M$^{-1}$cm$^{-1}$).

Iminothiolane dependent thiolation mediated PEG-maleimide based conservative PEGylation of HbA. HbA (0.5 mM tetramer) in phosphate buffered saline (PBS) was reacted with a desired level of molar excess of iminothiolane (Bio-Affinity systems) at 4° C. (or at room temperature) with in the presence of a 2 fold molar excess of Mailed Phenyl carbamate of PEG-5000 (BioAffinity System) or Mailed Ethyl PEG-5000 (Shearwaters) or Mailed Phenyl carbamate of PEG-1000 over that of iminothiolane for a desired period of time. The reaction at 4° C. is preferred over that at room temperature, since at room temperature some amount of oxidation of thiol groups of thiolated Hb appears to takes place even in the presence of PEG-maleimide, and this is considerably reduced at 4° C. The PEGylation reaction is generally carried out at a protein concentration of 0.5 mM, but it could also be carried out using a Hb concentration of either 0.25 mM or of 1 mM Hb.

The thiolation mediated PEGylation has also been studied as a two step reactions, first thiolation of Hb is carried out by incubating Hb with the desired excess of iminothiolane and then desired molar excess (over that of iminothiolane) of PEG-maleimide was added to achieve the PEG modification of the thiolated Hb.

For the generation of non-hypertensive Hb, thiolation with 10 fold molar excess over Hb (expressed as tetramer) and PEGylation of the thiolated protein with a 20 fold molar excess of desired PEG-maleimide was used. This is generally carried out as a one step reaction to reduce the oxidation of the thiol groups. If the reaction is carried out at room temperature, generally a 4 to six hour reaction time is needed to get the desired molecule. When the reaction is carried out at 4° C., usually overnight reaction (~16 hrs) is carried out.

The surface decoration of Hb by the thiolation mediated PEG-maleimide based PEGylation using Mal-Phe-PEG-10,000 has been carried at a protein concentration of 0.25 mM since the reaction at higher concentration of Hb leads to incomplete reaction, presumably due to the higher viscosity of the reaction mixture when a 20 fold molar excess of Mal-PEG-2000 was used.

The reaction products are dialyzed extensively against PBS using a dialysis tubing with a cut off of 12 to 14,000 daltons. The unreacted (excess PEG-maleimide) is dialyzed out; the PEGylated products were purified by size exclusion chromatography using Superose 12 column connected to Pharmacia Acta. The PEGylated Hb thus isolated, (PEG5K)$_6$-Hb is stored at −80° C. till needed further.

Measurement of size Enhancement on thiolation mediated PEG-maleimide based PEGylation. Analysis or the size enhancement of Hb as a function various thiolation mediated PEG-maleimide based conservative PEGylation was carried out using a Pharmacia FPLC system. Size-exclusion chromatography was carried out using 2 Superose columns connected in series. Samples were eluted using PBS at pH 7.4 and a flow rate of 0.5 ml/min at room temperature at 300.15 MHZ at 29° C. using a 5 mm probe. The Hb samples were 4 to 7% concentration in 0.1 M

II. Results

Figure 2A:
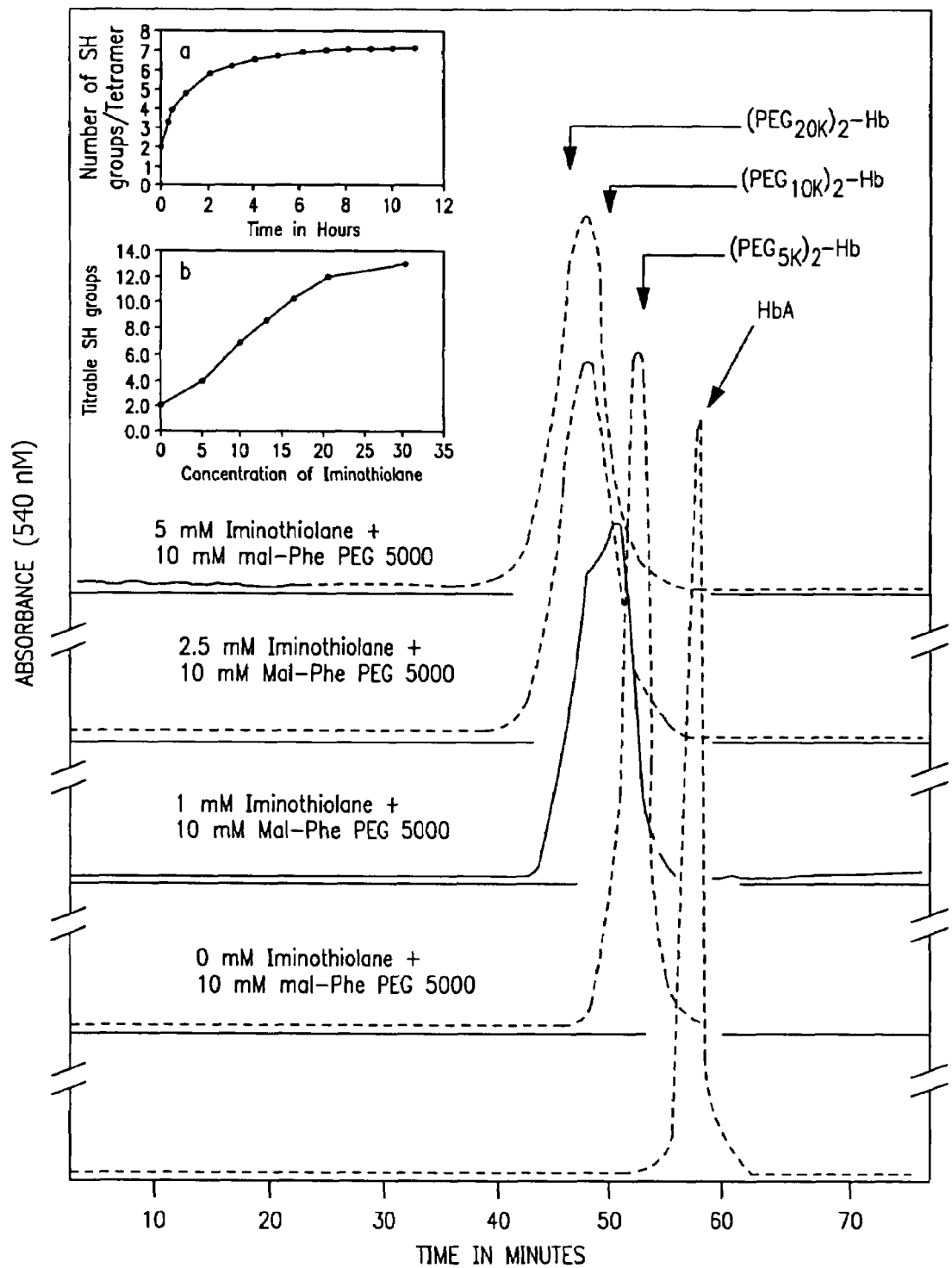
FIG. 2 depicts thiolation mediated PEG-maleimide based PEGylation of Hb. A: Influence of iminothiolane on the size enhancement of Hb on incubation with maleidophenyl PEG-5000. Hb (0.5 mm in tetramer0) in PBS pH 7.4 is incubated with 10 mM maleidophenyl PEG-5000 for 4 hours at 4° C. either in the presence or in the absence of a known concentration of iminothiolane. The products were analyzed by size exclusion chromatography by FPLC using two superose columns connected in series. The column was eluted with PBS at a flow rate of 0.5 ml per minute. The elution positions of HbA, $(PEG_{5K})_2$-Hb, $(PEG_{10K})_2$-Hb and $(PEG_{20K})_2$-Hb are marked as guide to follow the size enhancement of the hb molecule that accompanies the conjugation of PEG-chains. 1: Control Hb 2: HbA incubated with 10 mM maleidophenyl PEG-5000 for 4 hour in the absence of iminothiolane. 3: PEGylation in the presence of 1 mM (two fold molar excess) iminothiolane. 4: PEGylation in the presence of 2.5 mm iminothiolane (5 fold molar excess). 5:PEGylation in the presence of 5 mM iminothiolane (10 fold molar excess). The kinetics of thiolation of Hb in the presence of a 10 fold molar excess of iminothiolane (over that of Hb) is given in inset a. The inset b shows the extent of thiolation of Hb (after 4 hours of incubation) as a function of the molar excess of iminothiolane over Hb. B: Influence of the temperature, molecular size of PEG in PEG-maleimide and linker chmistry (the linkage between PEG and maleimide moiety) on the size enhancement of Hb. All PEGylation reactions are carried out using 10 fold molar excess of iminothiolane and 20 fold molar excess of PEG-maleimide for 4 hours at room temperature and for overnight at 4° C. The size enhancement was assayed by size exclusion chromatography as explained under A. a: HbA, b: Reaction at room temperature using Mal-Phe-PEG-5000 as the PEG maleirnide. c: Reaction as in b using Mal-Phe-PEG-10,000. d: Reaction as in b, but carried out at 4° C. for overnight. e; Reaction as in d, but carried out using maleimido ethyl PEG-5000 as the PEG-maleimide.

A) Development of the Conservative PEGylation Technology (i) Increase in the hydrodynamic volume of HbA as a result of thiolation mediated, maleimide chemistry based PEGylation of Hb. The size exclusion chromatographic pattern of Hb when it is incubated with a 20 fold molar excess of Mal-Phe-PEG$_{5K}$ for 4½ hours at room temperature in the absence and presence of iminothiolane is shown in FIG. 2A. In the absence of iminothiolane itself, Hb is completely modified with PEG-Phe-PEG-5000 (FIG. 2A, b). The unmodified Hb elutes around 57 minutes (FIG. 2A, a), whereas HbA incubated with Mal-Phe-PEG 5K elutes around 50 minutes. The elution position of this product corresponds to Hb modified at its two Cys-93(β) with Mal-Phe-PEG$_{5K}$,. The elution positions of (SP-PEG$_{10K}$)$_2$-HbA as well as of (SP-PEG$_{20K}$)$_2$-HbA, with the respective PEG-chains linked at Cys-93(β) is around 47 and 44 minutes on this column and marked for reference.

On inclusion of iminothiolane in the reaction mixture Hb with Mal-Phe-PEG 5K, the modified Hb eluted earlier than the position of (PEG$_{5K}$)$_2$-HbA from the size exclusion chromatographic column. New PEG-maleimide sites have been, apparently generated, thereby providing new PEG-maleimide reactive sites on Hb. The modified Hb(PEGylated Hb) eluted earlier on the size exclusion chromatography in a iminothiolane concentration dependent fashion. The higher the concentration of iminothiolane, the earlier is the elution position of the modified Hb, suggesting that the increased levels of thiolation of Hb as function of the increased concentration of the iminothiolane in the reaction mixture is responsible for the increased apparent molecular size of Hb. The PEGylated Hb generated in the presence of 2.5 mM iminothiolane (5 fold molar excess per tetramer) elutes at a position close to that of (SP-PEG$_{10K}$)$_2$-HbA (FIG. 2A, d). The sample formed in the presence of 5 mM iminothiolane, elutes very close to the position of (SP-PEG$_{20K}$)$_2$-HbA, but appear to have hydrodynamic volume that is slightly smaller that of as that of (SP-PEG$_{20K}$)$_2$-HbA (FIG. 2A, e). However this material has a small shoulder on the ascending side of the peak.

On increasing the iminothiolane concentration further to 7.5 mM without changing the concentration of Mal-Phe-PEG the same (10 mM), the elution pattern of the PEGylated Hb peak become slightly broader, but only a small increase in the yield of the product eluting as a shoulder (data not shown). Even on increasing the concentration of iminothiolane to 10 mM the elution pattern did not change significantly, except for small changes in the concentration of the shoulder on the ascending side.

The influence of the concentration of PEG on the shoulder on the ascending side has also been studies as a function of increasing concentration of PEG-maleimide. This shoulder considerably reduced (almost disappeared) when the concentration of Mal-Phe-PEG is increased to nearly double the concentration used in FIG. 2e, had little influence on the elution position of the main peak.

The kinetics of thiolation of Hb by a 10 fold molar excess of iminothiolane is shown in FIG. 2A (inset a). On an average Hb thiolated with a 10 fold molar excess of iminothiolane carries ~7 reactive -SH groups (towards dithiopyridyl) per tramer, two of which are the intrinsic -SH groups of Cys-93 (β) and the rest the intrinsic thiol groups introduced by the reaction of iminothiolane with the reactive surface ε-amino groups of Hb (γ-mercapto bytyramidination of Hb). Since 10 fold molar excess of iminothiolane has been used, the efficiency of thiolation is nearly 50%. The PEGylated Hb had about 0.5 moles reactive thiols per tetramer (under non-denaturing conditions), which suggests that, on an average, nearly ~6.5 copies of PEG-chain are introduced on to Hb in generating this PEGylated Hb.

The thiolation of Hb has also been studied as a function of the iminothiolane concentration at a protein concentration of 0.5 mM (FIG. 2A. Inset b). Increasing the concentration of iminothiolane from 10 fold molar excess, that introduced on an average five extrinsic thiols per tetramer, to 30 fold nearly doubled the number of the extrinsic thiols on the thiolated Hb. However, the size enhancement seen on PEGylation is only marginal, which suggested that the PEGylated Hb is unable to react at all the extrinsic thiols of the thiolated Hb. These results have been interpreted as suggesting that the PEGylation Hb in the presence of 10 fold molar excess of iminothiolane and 20 fold molar excess of Mal-Phe-PEG$_{5K}$ covers the surface Hb molecule significantly creating a 'crowding situation' wherein the thiolated Hb at this stage of PEG of enhancing the molecular size of Hb by this thiolation mediated, PEG-5000 maleimide dependent PEGylation becomes more resistant for modification of the additional extrinsic thiols of the PEGylated Hb. Accordingly, for all the subsequent studies, PEGylated Hb generated by surface decoration of Hb with PEG was using ten fold excess of iminothiolane (over the protein as tetramer) in the presence of 20 fold molar excess of Mal-Phe-5000 PEG has been used.

Figure 2B:
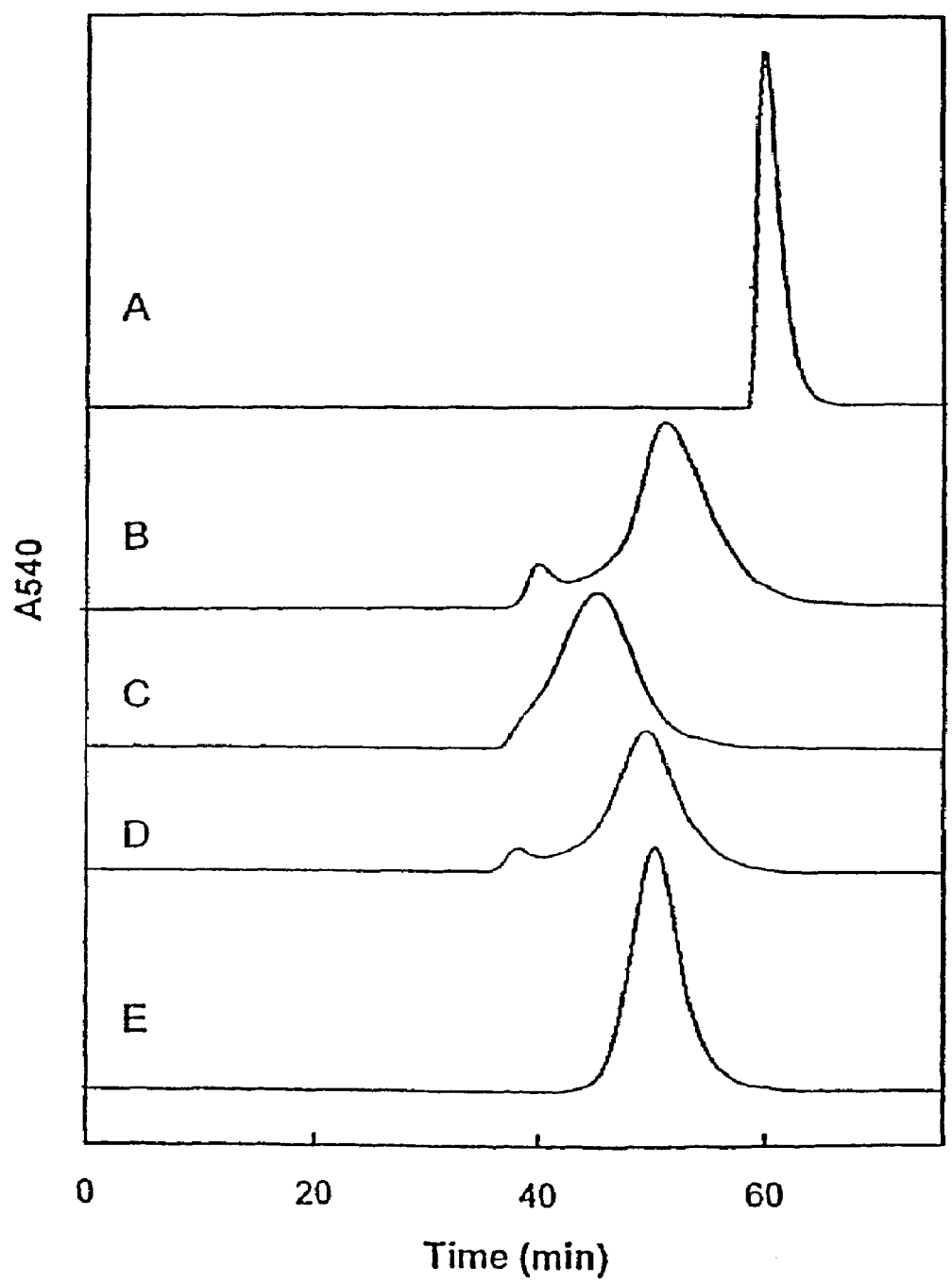

(ii) Flexibility in the thiolation mediated Maleimide-PEG based PEG modification of Hb. Influence of temperature, pH, linker chemistry, and the molecular size of the PEG in the PEG-maleimide has been investigated on the formation of (PEG-5K)$_6$-HbA, using 10 fold molar excess of iminothiolane and 20 fold molar excess of PEG-maleimide and the size exclusion chromatography on Superose 12 columns as the assay system. When the temperature is lowered to 4° C. the rate of the attachment of the PEG-chains to thiolated protein appears to be slowed down, but rate of thiolation of Hb was not influenced to great degree, carrying out the reaction up to 9 hrs ensured the completion of the reaction, but routinely overnight reaction (14 to 6 hrs) was chosen as a matter of convenience (FIG. 2B, curve c). Carrying out the PEGylation as a two step process, first thiolating and then PEGylating also did not appear to influence the size enhancement (data not shown). The surface decoration with PEG has been carried out at three pH values, pH 6.5, 7.4 and 8.5. The PEGylated products formed at pHs 6.5, 7.5 and 8.5 using 10 mM phosphate buffer has been compared with that established at pH 7.4 in PBS. All the products are comparable in terms of the size enhancement achieved by surface decoration.

The size enhancement seen on surface decoration with PEG-5000 was also independent of the linker chemistry, the reaction products obtained using Mailed-phenyl-PEG-5000 had essentially same hydrodynamic volume as that generated with PEG-Ethyl-PEG-5000 (FIG. 2B, curve d). The size enhancement of Hb, under a given set of thiolation condition, is sensitive to the molecular size of the PEG in the PEG-Maleimide. On increasing to mass of the PEG-chain to 10,000 from 5000, the size enhancement seen is higher than that seen with PEG-5000 maleimide (FIG. 2B, curve e).

(iii) Purification of (PEG$_5$)$_6$-HbA. For generation of materials up to a gm of (PEG)$_6$-HbA, a gel filtration protocol has been developed. Routinely HbA (0.5 mm) is incubated with a ten fold molar excess of iminothiolane and 20 fold molar excess in phosphate buffer saline (pH 7.4)for four to six hours and then the reaction mixture was subjected to three changes of dialysis against 100 fold excess of PBS to remove the excess (un-reacted) iminothiolane and maleimide PEG. The dialyzed sample was concentrated to about 1 mm and subjected to gel filtration using preparative Superose 12 column connected to an Pharmacia Acta Explorer 10. A typical chromatographic profile of a sample of HbA PEGylated under the conditions discussed above is shown in FIG. 6A. The elution was monitored at three wavelengths, to facilitate the monitoring of the elution of any PEG-maleimide that has not reacted with Hb. The PEGylated Hb elutes much ahead of the un-reacted PEG-maleirnide present in the sample. The gel filtered PEGylated sample was concentrated to about 6 gms/dL. HbA does not undergo any detectable autooxidation to generate met-Hb type of products either during the thiolation mediated maleimide chemistry based PEGylation reaction or during the subsequent purification steps. The sample of PEGylated Hb can be stored at −80° C. without undergoing any autooxidation for periods up to at least up to one year.

Figure 3:
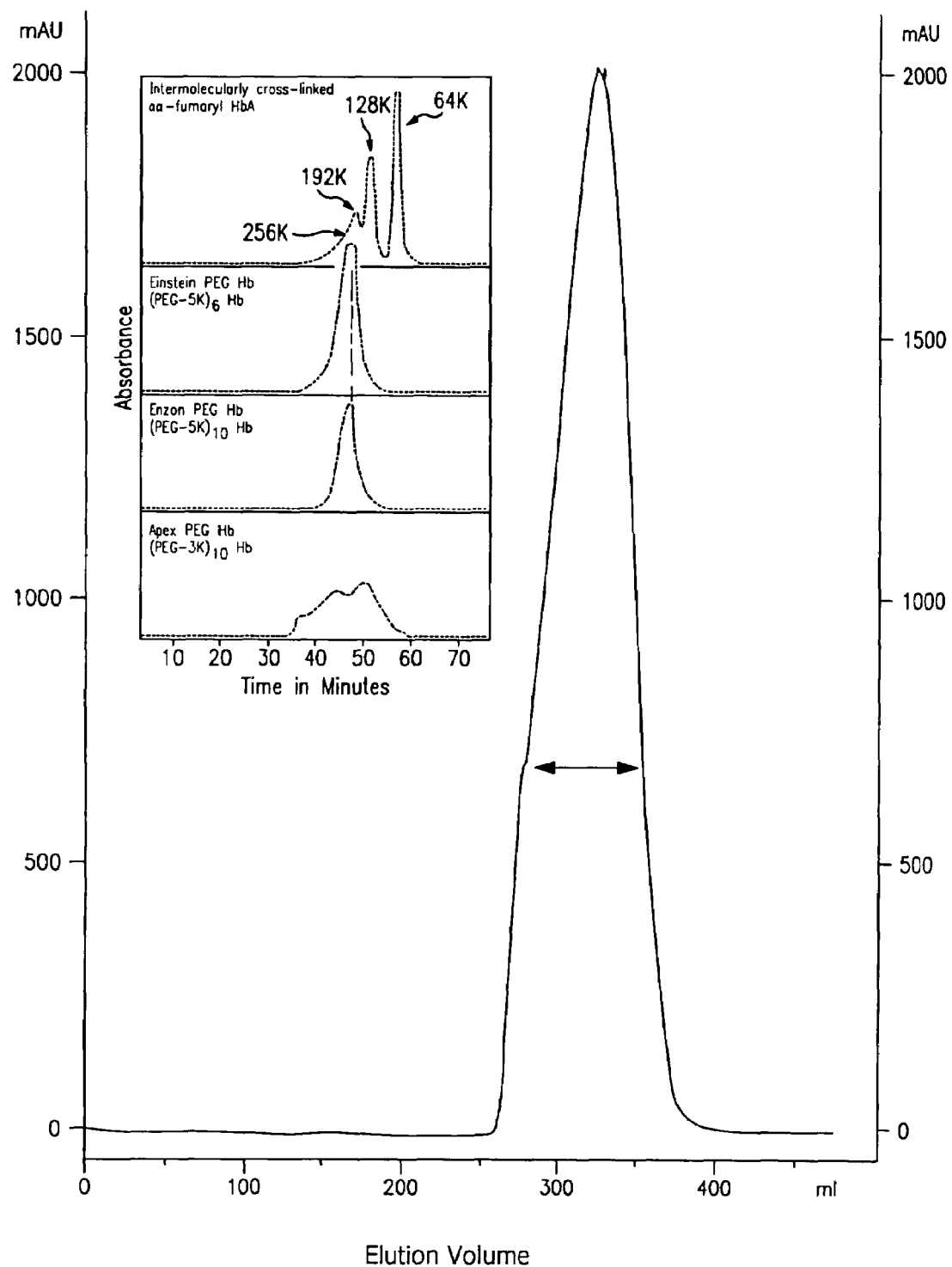
FIG. 3 depicts the purification of $(PEG_{5K})_6$-Hb by size exclusion chromatography using Acta explorer. The preparative scale experiments were carried out with a 180 mg load. The elution was carried out using PBS as done with the analytical scale experiments (FIG. 2). The PEGylation was carried out at 4° C. using a 10 fold molar excess of iminothiolane and 20 fold molar excess of Mal-Phe-PEG-5000. The inset compares the molecular size of the purified $(PEG_{5K})_6$-Hb with that of other PEGylated Hbs and of $\alpha\alpha$ fumaryl Hb (an intramolecularly crosslinked Hb) inter tetramerically crosslinked using bis maleidophenyl PEG-600. This samples helps to mark the position of tetrameric, octomeric, dodecameric and dohexameric forms of $\alpha\alpha$-fumaryl Hb. 1: intertetramerically crosslinked $\alpha\alpha$-fumaryl Hb, 2: $(PEG_{5K})_6$-Hb purified on Superose-12 preparative column. 3: Enzon PEGylated Hb; $(PEG_{5K})_{10}$-Hb 4: PEGylated Hb sample of APEX Biosciences, $(PEG_{3K})_{10}$-Hb.

(iv) Quantitation of the Size Enhancement of Hb resulting from Conservative PEGylation of Hb. The elution pattern of purified (PEG-5K)$_6$-Hb has been compared with that of αα-fumaryl Hb intertetramerically crossbridged using Bis maleidophenyl PEG-600. (FIG. 3, inset, b and a). As noted earlier, the conservatively, PEGylated Hb, (PEG-5K)$_6$-Hb, is slightly smaller than, (PEG$_{20K}$)$_2$-HbA, and higher than that of (PEG$_{10K}$)$_2$-HbA. Its hydrodynamic volume appears to correspond to that of a globular protein with a molecular mass of about 250,000 daltons. Since the PEG-mass on this is ~30,000, and thus the calculated molecular mass is only 95,000 daltons. But its hydrodynamic volume corresponds to that of a protein of a molecular mass of 250,000. Thus, incorporation of a mass of 30,000 on to Hb as six copies of PEG-5000 chains is equivalent to incorporating nearly 180,000 mass of globular protein on to Hb. Thus, PEG exhibits a potential to increase the hydrodynamic volume of Hb that is nearly six times that of a tightly packed globular protein. This conclusion is similar to of that Manjula et al (2002) have drawn recently from their PEGylation studies wherein the site of PEGylation was restricted to Cys-93(β), the size enhancement was achieved as a function of the molecular size of PEG in the PEG-maleimide used. Thus the size enhancement that is occurring as a result of PEGylation appears to be a direct correlate of total PEG-mass linked to Hb, and is additive when the PEG-mass is presented as different number of copies.

The size exclusion chromatographic pattern of (PEG$_{5K}$)$_6$-HbA generated by the new thiolation mediated maleimide chemistry based PEGylation protocol has been compared with that of Enzon (PEG$_{5K}$)$_{10}$-Bv-Hb, a non-vasoactive PEGylated Hb (FIG. 3 inset, curve c). This material is also pretty homogeneous in terms of the molecular size distribution just as the (PEG-5K)$_6$-Hb. This PEGylated Hb has ten copies of PEG-5000 (total PEG-mass of 50,000) per tetramer and is accordingly anticipated to have a higher size enhancement as compared to (PEG-5K)$_6$-Hb. However, the size enhancement seen with this Hb is not as much as that seen with (PEG-5K)$_6$-Hb. The molecular basis for this anomaly is not readily apparent at this stage. On the other hand, PHP, another PEGylated Hb that carries 10 copies of PEG-3000 per tetramer, should be expected to have a hydrodynamic volume comparable to that of $(PEG-5K)_6$-Hb given the fact the amount of PEG mass per tetramer in this product is comparable to that in $(PEG-5K)_6$-Hb. PHP is very heterogeneous (FIG. 3 inset, curve d). It carries some amounts of material that has a size enhancement smaller than that of $(PEG-5K)_6$-Hb, and some material with a size enhancement comparable to that of $(PEG-5K)_6$-Hb, and some bigger than that of $(PEG-5K)_6$-Hb. The use of bifunctional PEG-3000 for surface decoration, and the intra and or inter tetrameric crosslinks present in this sample may have contributed to the high level of heterogeneity in the PHP.

B) Molecular, Colligative and Functional Characterization of $(PEG_5)_6$-HbA.

Figure 4:
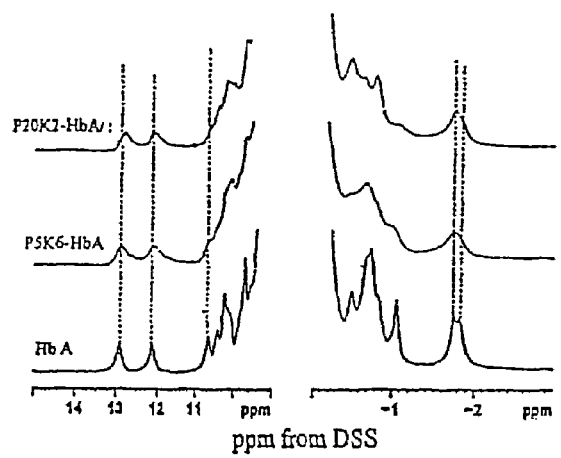
FIG. 4 depicts the NMR Spectra of $(PEG_{5K})_6$-Hb.
Figure 4:
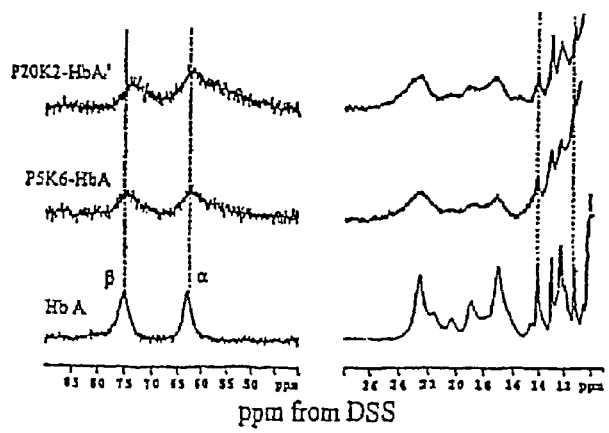

(i) $^1$H-NMR spectroscopy of $(PEG_5)_6$-HbA. Proton nuclear magnetic resonance spectroscopy of Hb is an excellent tool for monitoring the changes in the tertiary and quaternary structure of HbA that accompanies either chemical modifications or mutation at any given sight. The location of the Cys-93(β) is in a conformational sensitive region of the molecule, and the reactivity of Cys-93(β) towards the sulfhydryl specific reagents is a unique feature of the oxy conformation of the molecule, in the deoxy structure it is unreactive. FIG. 4A compares the proton NMR spectra of $(PEG_{20})_2$-HbA and $(PEG_5)_6$-HbA with that of HbA in 0.1 M phosphate buffer at pH 7.0 and 29° C. in both carbonmonoxy and deoxy forms. These two samples nearly the same amount of PEG-mass per tetramer [40,000 in $(PEG_{20})_2$-HbA vs 30,000 in $(PEG_5)_6$-HbA ]. With the exception of broader resonances observed with PEGylated samples due to an increase in the molecular size as a result of PEGylation of Hb, there is no significant differences in the chemical shift over which spectral region of 10 to 14 ppm indicating no alterations in the $\alpha_1\beta_1$ interface of the protein as a result of the PEGylation of Hb either only at Cys-93(β) using PEG-20,000 or at Cys-93(β) and at least four other ε-amino groups of Hb using PEG-5000. FIG. 4B compares the ring-current-shifted proton resonances of the two PEGylated Hbs with that of HbA in the carbonmonoxy form. There are some alterations in the ring current shifted proton resonances reflecting some perturbation in the micro environment of heme of PEGylated Hb-samples. FIG. 4C shows the hyperfine shifted $N_\delta H^1$-resonances of proximal histidine residues of α and the β-chains of PEGylated Hbs in the deoxy form. The chemical shift at −75 ppm assigned to $N_\delta H$ of the proximal histidine of the β-chain is shifted upfield by −2 to −3 ppm reflecting the perturbation of the β-heme environment in the PEGylated samples. This upfield shift is some what more pronounced in $(PEG_{20})_2$-HbA than in that of $(PEG_5)_6$-HbA. FIG. 5D compares the hyperfine shifted and exchangeable proton resonances of the two PEGylated samples of HbA with that of HbA in the deoxy form. The hyperfine shifted resonances are broader that of HbA. Besides there are some changes in the resonances in the spectral region from 16 to 24 ppm, reflecting changes in the microenvironment of β-heme of Hb as a result of PEGylation of the molecule. The resonance at 14 ppm, assigned to an important H-bond between α-Tyr(42) and β-Asp(99) in the $\alpha_1\beta_2$ subunit interface is unchanged in the PEGylated samples. Thus, there are no changes in the $\alpha_1\beta_2$ subunit interface of the PEGylated Hb.

(ii) Molecular radius of the $(PEG_5)_6$-HbA. The molecular radius of $(PEG_5)_6$-HbA has been determined by dynamic light scattering and compared with that of $(PEG_5)_2$-HbA, and $(PEG_{20})$-HbA that we have measured previously (see, Table I). The molecular radius of $(PEG_5)_6$-HbA is around 6.8 nm. This molecular radius is slightly smaller that of $(PEG_{20})_2$HbA, which has been previously estimated to be 7.04. The values for $(PEG_5)_2$-HbA and HbA are 4.2 and 3.1 respectively. Thus the molecular radius of HbA is more than doubled when surface decorated with about six copies of PEG-5K chains, even though the mass added onto the protein is only around 30,000. Thus $(PEG_5)_6$-Hb exhibits an enhanced molecular size that expected for a globular protein of molecular weight 94,000, and the packing of the PEG in this size enhanced region of Hb is not as dense as in the protein core. The molecular radius of Enzon PEG Bv-Hb, that has a molecular mass of 114,000, has a molecular radius smaller than that of $(PEG_5)_6$-Hb, 5.53 nm and is close to that of $(PEG-10K)_2$-HbA and $(PEG-5K)_4$-Dog Hb. It may also be noted that the molecular radius of $(PEG_5)_6$-Hb generated using Mal Ethyl PEG-5000 is nearly 10% smaller than the one generated using Mal-Phe-5000. The molecular radius of $(PEG-10K)_6$-Hb is around 9.8, thus establishing the need to use higher molecular size PEG to get PEGylated Hb with molecular radius larger than 7 nm gotten with $(PEG-5K)_6$-HbA.

(iii) Comparison of the Molecular density of PEGylated Hb generated by conservative and non-conservative PEGylation protocols. Since the size enhancement (increase in the hydrodynamic volume) that is achieved by PEGylation is nearly six times more efficient than that in a globular protein (on an equal mass basis), implies that the molecular density of atoms in the enhanced volume of PEGylated Hb is low as compared to that in compact globular proteins. The molecular density of PEG in the enhanced molecular volume of various PEGylated Hb is also given in Table 1. The molecular density of PEG in the enhanced molecular volume of Hb decreases by nearly 50% as the molecular mass of PEG linked to Cys-93(β) of increases from 5000 to 20,000. A decrease in the molecular density implies a decreased interaction between the PEG-chains and an increased occupancy of the solvent molecules within the PEG-shell of a given PEGylated Hb. When the PEG density in the PEG-shell is low, it could be considered as present in a 'mushroom conformation', while the density is high in the PEG-shell, it could be considered as being present 'in the brush border conformation' and in $(PEG_5)_6$-Hb, the molecular density of PEG-shell is even smaller than that in $(PEG_{20})_2$-Hb. On the other hand, the molecular density of the PEG-shell of Enzon PEG Bv-Hb is very high, suggesting that the interactions between the PEG-chains within the PEG-shell is stronger as compared to that in the PEG-shell of $(PEG_5)_6$-Hb. The studies clearly reflect the differences in the packing of the PEG-chains between the Enzon PEGylated Hb and the new PEGylated Hb generated by the conservative PEGylation Technology. The sample generated by the conservative PEGylation can be considered as being present on a 'mushroom conformation' and the Enzon PEGylated sample in a brush border like conformation'.

Figure 5:
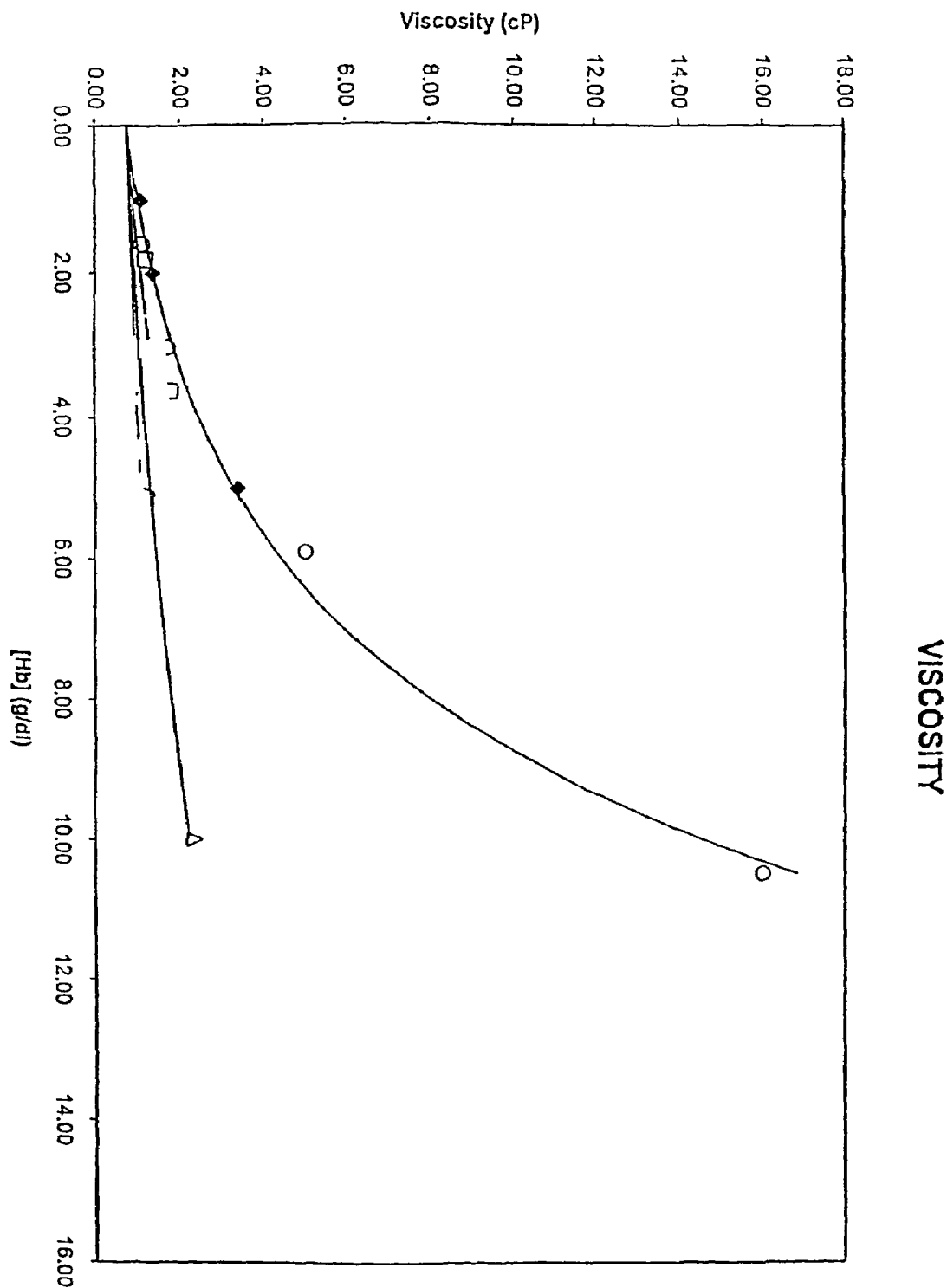
FIG. 5 depicts the viscosity of PEGylated Hb as function of the protein concentration. The open circles represent $(PEG_{5K})_6$-Hb; the filled diamond represent the Enzon PEGylated Hb and the open triangles represent the $(PEG_{5K})_2$-Hb.

(iv) Colligative properties of $(PEG_5)_6$-HbA. FIG. 5 compares the viscosity of $(PEG_5)_2$-HbA and $(PEG_5)_6$-HbA as function of protein concentration in the range of 1 to 10 gm/dl. The viscosity of $(PEG_5)_2$-HbA showed only a small increase in the viscosity, as the concentration of the protein increased from 1 gm/dl to 10 gm/dl, and viscosity of the PEGylated solution appears to be directly proportional to the concentration of the protein. On the other hand even though the viscosity of the solution of $(PEG_5)_6$-HbA in comparable to that of $(PEG_5)_2$-HbA in very dilute solutions (1 gm/dl), the viscosity of the former increased exponentially with the concentration of the protein. Viscosity of Enzon PEG bovine Hb that carries 10 equivalents of PEG-5K chains (to the α and ε-$NH_2$ of bovine Hb through isopeptide linkages) in the concentration range of 1 to 5 gm/dl is also shown for comparison. At all the concentrations studied, the viscosity of Enzon PEG bovine Hb is comparable to that of the viscosity of $(PEG_5)_6$-

HbA. The results suggest that either the chemical nature of the linkage and sites of PEGylation has a strong influence on the PEGylation or a viscosity of a solution of PEGylated Hb reaches a saturation value with the presence of six copies of PEG-5K chain per tetramer.

Figure 6:
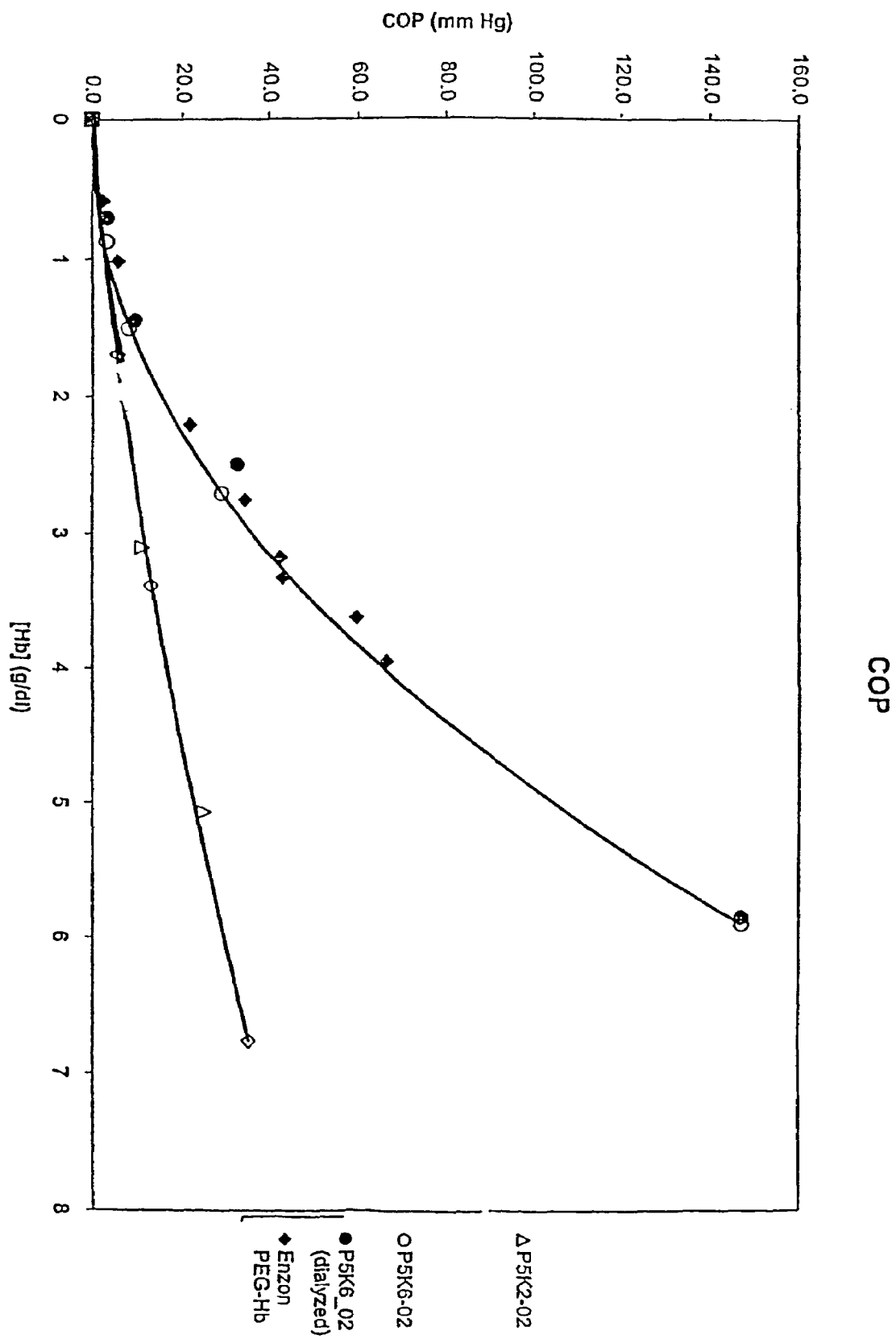
FIG. 6 depicts the colloidal osmotic pressure of $(PEG_{5K})_6$-Hb as a function of protein concentration. The open triangle represents $(PEG_{5K})_2$-Hb, open circles represent $(PEG_{5K})_6$-Hb; the closed circles represent the $(PEG_{5K})_6$-Hb that has been redialyzed to ensure that the sample is devoid of any free PEG reagent. The closed diamond represents the Enzon PEGylated Hb. Note that the colloidal osmotic pressure of Enzon PEG-Hb and $(PEG_{5K})_6$-Hb are comparable.

The colloidal oncotic pressure of samples of PEGylated Hb as a function of the protein concentration is shown in FIG. 6. The oncotic pressure of the sample increased as a function the protein concentration. This increase is small with $(PEG_5)_2$-HbA, and appears to increase linearly with the protein concentration (in the range of 1 to 6.8 gm/dl). On the other hand the oncotic pressure of solutions of $(PEG_5)_6$-HbA increased exponentially as the concentration of the protein increased. Again when the concentrations are matched, the oncotic pressure of Enzon $(PEG_5)_{10}$-Bv-Hb is comparable to that of $(PEG_5)_6$-HbA. The results suggest that the oncotic pressure of a sample of PEGylated Hb is a direct correlate of the viscosity of that sample.

(v) Functional properties of $(PEG_5)_6$-HbA. The oxygen affinity of $(PEG_5)_6$-HbA in 50 mM Bis-Tris/50 mM Tris acetate, pH 7.4 and 37° C. and its modulation in the presence of allosteric effectors is shown in Table I. The $P_{50}$ of Hb is lowered (an increased oxygen affinity) PEGylation of HbA, from the control value of 8.0 to 6.5. The presence of five fold excess of DPG, an effector that lowers the oxygen affinity of HbA by binding at the ββ-cleft had no significant influence on the oxygen affinity. On the other hand the presence 1 M sodium chloride lowered the oxygen affinity of the PEGylated slightly ($P_{50}$ increased from 6.5 to 8.5), and is comparable to that of unmodified HbA in the absence of chloride. The oxygen affinity of unmodified Hb, on the other hand, is lowered significantly in the presence of 1.0 M chloride. In the presence of L-35.an allosteric effector that reduces the oxygen affinity of Hb by binding at the αα-end of the molecule increased the $P_{50}$ of $(PEG_5)_6$-HbA had some oxygen affinity reducing influence, however markedly reduced as compared to that seen with unmodified HbA. Thus, the thiolation mediated maleimide chemistry based PEGylation HbA has almost completely inhibited the propensity of HbA to respond to the presence of DPG, and drastically reduced the propensity of the molecule to respond to chloride and L-35.

The $O_2$ affinity of $(PEG_5)_6$-HbA has also been determined in PBS, as the value of the sample in circulation should be comparable to that in PBS. Even in PBS, $(PEG_5)_6$-HbA exhibits a higher oxygen affinity ($P_{50}$=9.5 mm of Hg) as compared to the control HbA ($P_{50}$=15 mm of Hg). The oxygen affinity of $(PEG_5)_6$-HbA is only slightly higher than that of $(PEG_5)_2$-HbA ($P_{50}$=11.8). Since $(PEG_5)_6$-HbA has its Cys-93(β) modified as in the $(PEG_5)_2$-HbA, besides additional modifications on the ε-$NH_2$ groups of the Lysine residues of HbA, the oxygen affinity results suggest that the thiolation mediated PEGylation of ε-amino groups of HbA by themselves do not significantly influence the oxygen affinity of Hb. Thiolation mediated surface decoration of HbA using Mailed-Ethyl-$PEG_{5K}$: The commercially available maleimide PEG-reagents have alkyl spacer link between the maleimide moiety and the PEG-chain. In an attempt to establish the generality of the new PEGylation procedure developed here to maleimide alkyl PEG reagents as well, we have now replaced Mal-Phe-$PEG_{5K}$-in the thiolation mediated maleimide chemistry based reaction with Mal-Ethyl-$PEG_{5K}$. The reaction of HbA with this PEG also proceeds as expected, except for a slightly lower efficiency of the reaction. The product generated and expected to carry on an average six PEG-chains [(SE-$PEG_{5K}$)$_6$-HbA gave a gel filtration pattern similar to that of (SP-$PEG_{5K}$)$_6$-HbA except for a somewhat retarded elution on gel filtration. Besides as shown in Table 2, the molecular radius of (SE-$PEG_{5K}$)$_6$-HbA is slightly smaller than that of (SP-$PEG_{5K}$)$_6$-HbA.

B. Hypertensive Activity of $(PEG_{5K})_6$-HbA.

Figure 7A:
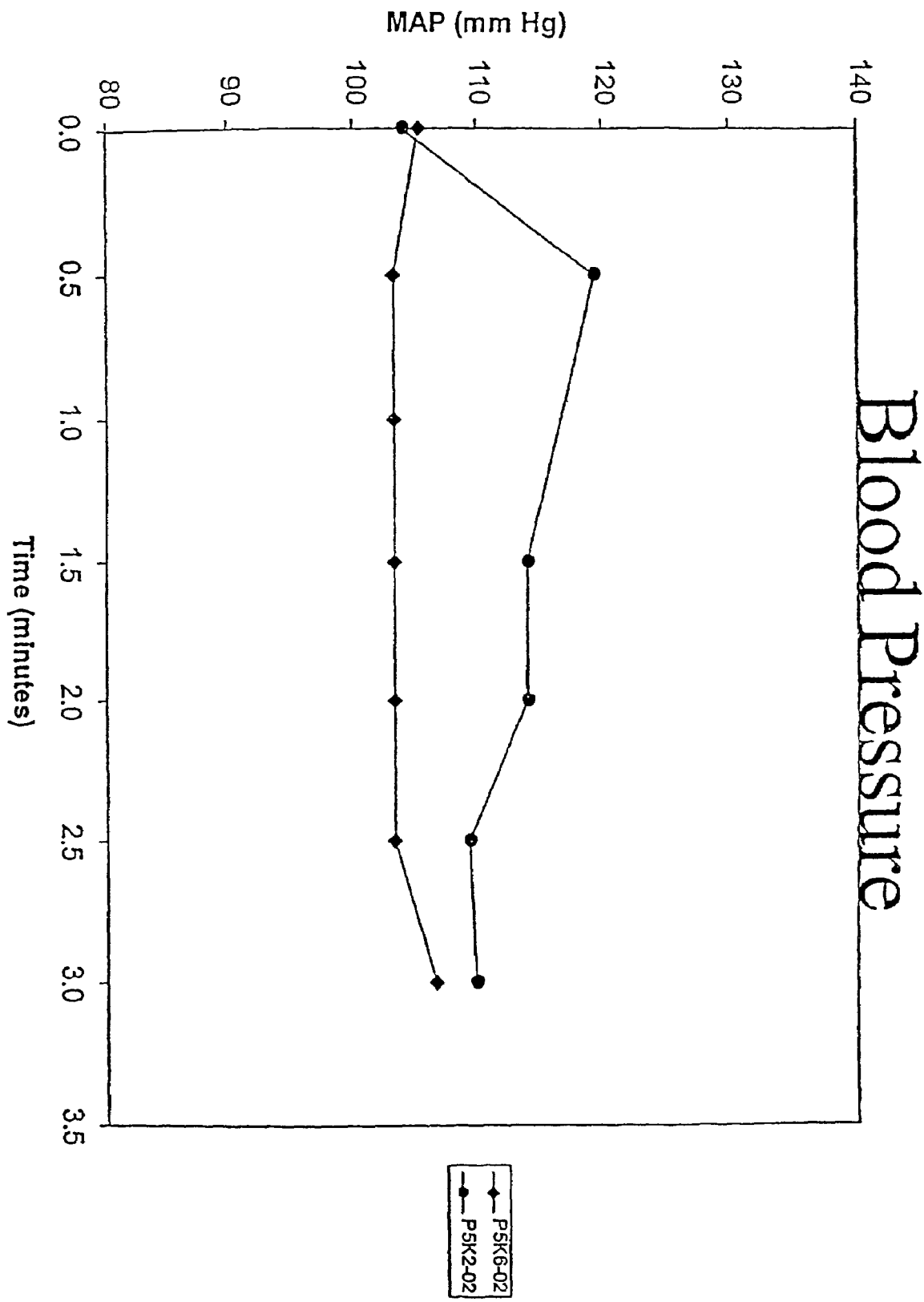
FIG. 7 depicts the vasoactivity of $(PEG_{5K})_6$-Hb. A: Mean arterial pressure. in hamster after the animal is infused with 10% top load of 4 gm % of $(PEG_{5K})_6$-Hb. B: The arteriolar diameter after the animal was infused with a 10% top load of $(PEG_{5K})_2$-Hb and of $(PEG_{5K})_6$-Hb as a function of time.
Figure 7B:
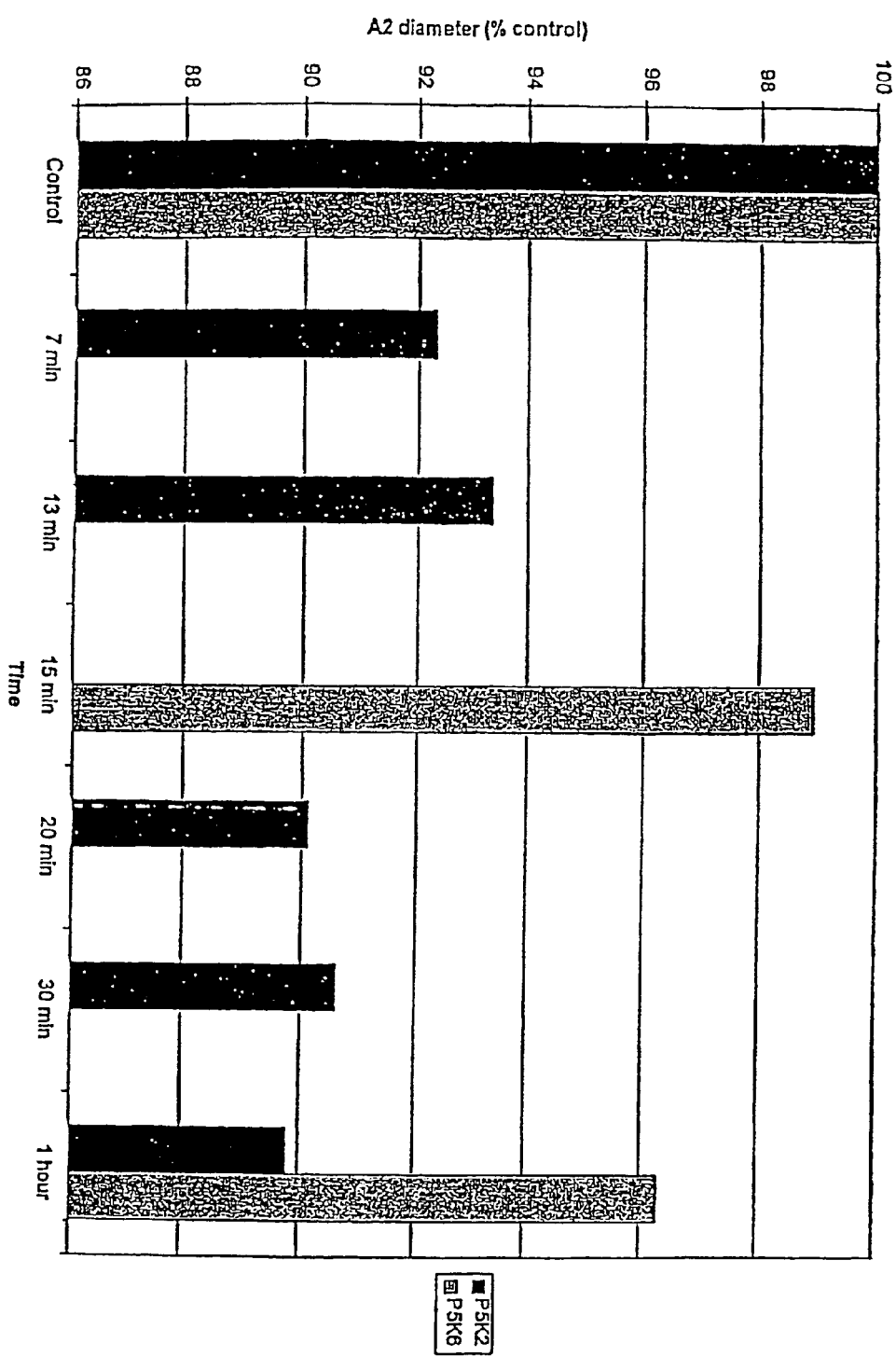

(i) Studies in Hamsters by 10% top load experiments. The changes in the vaso-constrictive activity of Hb on PEGylation with two and six copies of $PEG_{5K}$ chains has been investigated by in 10% top load experiment in hamster skin fold-window model by measuring the mean arterial pressure as well as by measuring the arteriolar diameter ($A_2$). As seen in FIG. 7A, infusion of $(PEG_{5K})_2$-HbA caused an immediate increase in the blood pressure that resolved within minutes. On the other hand, the sample of $(PEG_{5K})_6$-HbA caused no change in the blood pressure during the same period. The FIG. 7B compares the diameter of the artery after various periods of infusion of the hamster with a ten per cent top load of solutions of $(PEG_{5K})_2$-HbA and $(PEG_{5K})_6$-HbA. The sample of $(PEG_{5K})_6$-HbA conserves the alveolar diameter much more closer to the starting value than that by the sample of $(PEG_{5K})_2$-HbA. These analysis confirm that the PEGylation of acellular Hb, to a level of six copies of $PEG_{5K}$ chains inhibits the intrinsic vasoactivity of acellular Hb to a significant level.

Figure 8:
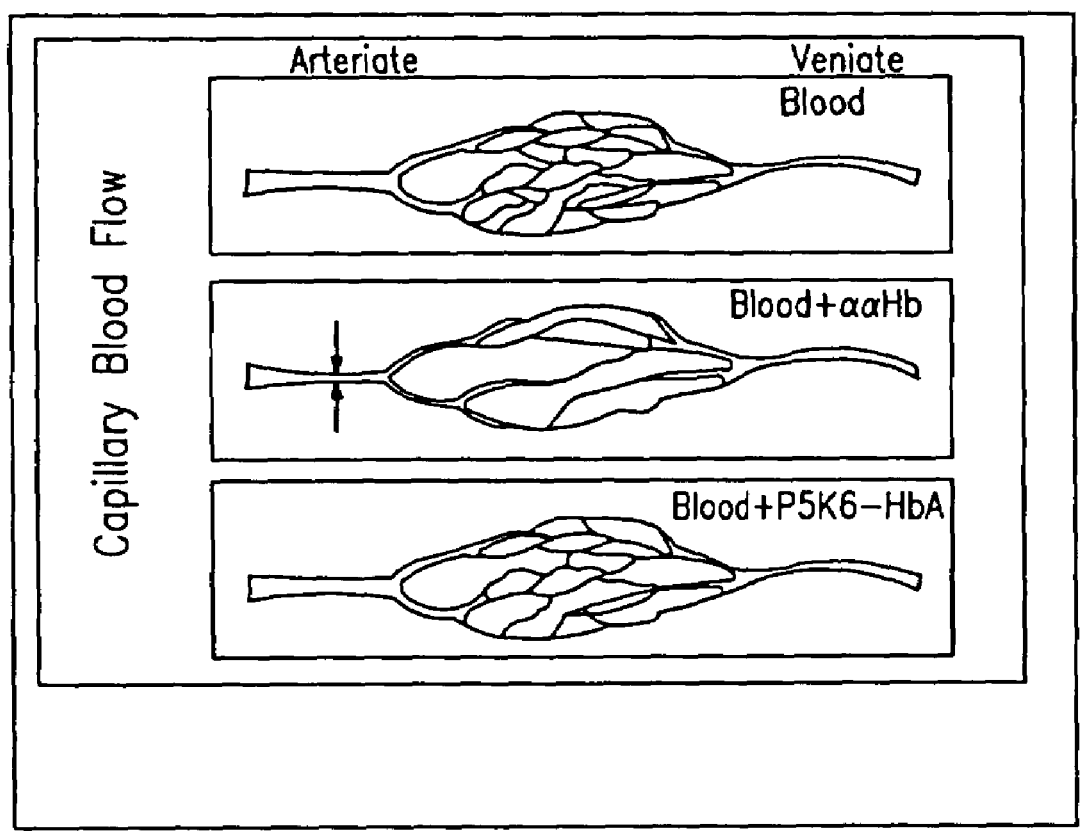
FIG. 8 depicts a comparison of the functional capillary density in hamster after the animals are 50% exchange transfused with $(PEG_{5K})_6$-Hb and $\alpha\alpha$-fumaryl Hb with that of control. Note that the diameter of the artery in the animal exchange transfused with $(PEG_{5K})_6$-Hb is comparable to that of the control sample, while that in the animal 50% exchange transfused $\alpha\alpha$-fumaryl Hb is narrower that in the control. Also note the differences in the capillary densities exchange transfused with the two samples.

(ii) Influence of 50% exchange transfusion with $(PEG_{5K})_6$-HbA on the functional capillary density in hamsters. The FIG. 8 depicts the capillary blood flow in the hamster 50% exchange transfused with $(PEG_{5K})_6$-HbA and compares with that of control (without exchange transfusion) as well as with that 50% exchange transfused with αα-fumaryl HbA. Thus, it is clear that the hamsters 50% exchange transfused with $(PEG_{5K})_6$-HbA maintain a high capillary density whereas the αα-fumaryl HbA reduces the functional capillary density significantly. Thus, surface decoration of Hb with PEG-5000 chains can neutralize the intrinsic vaso-constrictive activity of acellular Hb.

III. Discussion

A new, simple and flexible protocol for enhancing the molecular size of Hb without altering the surface charge of the protein by PEGylation has been developed. This involves the activation of a set of ε-amino groups of Hb either in the oxy or deoxy conditions by reaction with iminothiolane as PEG maleimide reactive sites (thiolation) and then modifying the thiolated Hb with the desired PEG-maleimide. This approach has been optimized to generate a PEGylated Hb carrying six copies of PEG-5000, and this has been found to be non-hypertensive.

In the absence of iminothiolane, the PEGylation of Hb using PEG-maleimide under oxy conditions is restricted to the modification of Cys-93(β), i.e. two copies per tetramer. This PEGylated Hb exhibits a hydrodynamic volume comparable to that of globular protein with a molecular weight of 128 KDa. The four other cysteine residues are buried and not accessible for reaction with PEG maleimide under the reaction conditions used. The Cys-93(β) also become unavailable for reaction with PEG-maleimide.

Iminothiolane, activates some of the ε-amino groups of Hb as PEG-maleimide reactive sites in a iminothiolane concentration dependent fashion. Iminothiolane, the cyclized form of γ-mercapto bytyrimidate does not have carry free thiol, and generates the thiol group in situ once it reacts with the ε-amino groups. On its reaction with Hb, a set of amidate reactive ε-amino groups are derivaitized as the γ-mercapto butyrimidinyl moieties, with a free -SH group at the distal end. The intrinsic positive charge of the ε-amino group is conserved in this derivatized ε-amino groups. These new extrinsic thiol groups of the thiol groups are the sites targeted for attaching PEG-chains of desired molecular size functionalized as maleimides. However, other approaches of functionalizing PEG as maleimides that utilize an alkyl linker or alkylamide linker between PEG and maleimide are equally efficient PEGylating agents, i.e. the PEGylation reaction is maleimide chemistry based. This approach of PEGylation has thus the advantage of conserving the net charge of Hb in the PEGylated Hb.

Oxy Hb incubated with a ten fold molar excess of iminothiolane activates nearly five $\epsilon$-amino groups of Hb as PEG-maleimide reactive sites. When a 20 fold molar excess of PEG-maleimide present along with 10 fold molar excess of iminothiolane, a PEGylated product that has, on an average, six $PEG_{5K}$-chains are is generated [$(PEG_5)_6$-Hb]. Two of the six PEG-chains introduced are on the sulfhydryl groups of Cys-93($\beta$) and rest on the thiolated Lys residues of Hb. The Hb carrying six PEG-5000 chains appears to have developed a degree of resistance for introducing additional PEG-5000 chains. It is not clear at this stage whether this reflects a degree of a uniform surface coverage on the Hb, masking the thiol groups of other surface a-amino groups of Hb that are activated by iminothiolane from reacting with PEG-maleimide.

The calculated mass of $(PEG_5)_6$-Hb is ~94 Kda. However, in size exclusion chromatography, $(PEG_5)_6$-Hb behaves as though it molecular size of the order of 250 kDa. i.e. $(PEG_5)_6$-Hb exhibits a n hydrodynamic volume corresponding to that of a globular protein with a molecular mass of ~250 KDa. Thus on the molecular scale of globular proteins, PEG chains increase the hydrodynamic volume, molecular volume of Hb nearly six times that of a globular protein.

A correlation of an increase in the molecular volume of the PEGylated Hb generated earlier using PEG-maleimides with the ones generated in the present studies suggest with mass of the PEG used in endowing such a size enhancement, suggests that the packing of the PEG-chains within each product is distinct. In site specific PEGyalted products studies earlier, an increase in the molecular mass of the PEG-chains decreases the molecular density of PEG in the PEG-shell of size enhanced Hb molecules. This can be interpreted as the molecular size of the PEG-chains anchored at the two Cys-93($\beta$), these can interact with one another, thereby increasing the molecular volume with in which the PEG-chains exist in molecular motion (the PEG-she around the protein). When PEG-shell around Hb is generated by six PEG-5000 chains [two on Cys-93($\beta$) and the other four on iminothiolane activated $\alpha$-amino groups], appears to be access the maximum space for their molecular motions. Preliminary calculations with $(PEG_{10})_6$-Hb suggests that the molecular space within which the PEG-chains flex has a molecular density is comparable to the PEG-shell of $(PEG_5)_6$-Hb or may be even less dense compared to that of $(PEG_5)_6$-Hb.

A surprising observation is the fact that molecular density of PEG-shell of Enzon PEG Hb, is considerably higher than that in that of $(PEG_5)_6$-Hb. The two PEGylated Hb are assembled using two very distinct chemistry. The present PEGylation is carried out using a conservative protocol, thus the net charge of the Hb molecule is conserved in the PEGylated product, i.e. the hydrated shell of the protein should have been experience limited perturbation in the PEGylated Hb. The Enzon PEGylation is carried out using a nonconservative protocol wherein the original positive charge of $\alpha$ and a amino groups derivatized are not conserved in the final product. Therefore, this protocol can be anticipated to perturb the hydrated shell of the protein. What ever may be the molecular basis, the two approaches appears to have generated PEG-shells around Hb that have very different architecture (molecular density) of PEG-chains within the PEG-shell that is encaging the Hb molecule.

The molecular density of the PEG-shell of $(PEG_5)_6$-Hb generated using Mailed-ethyl-PEG-5000 is higher than that in the PEG-shell of $(PEG_5)_6$-Hb generated using Mailed phenyl PEG-5000, but not as high as the one of Enzon PEG-Hb. The chemistry of the PEG-chains at the anchoring site that depicts the conjugating linage and the spacer linkage between PEG and functionalizing group is in the three products, succinimido phenyl PEGylated Hb, succinmido ethyl PEGylated Hb and acetamido PEGylated Hb is presented has been compared below schematically. Both mailed phenyl PEGylated Hb and mailed ethyl PEGylated have an activation arm ($\gamma$-mercaptobutyrimidyl), conjugating group(succinimidyl) as the common molecule entities. The Mal-Phe-PEG reagent has an phenyl ethyl carbamate as the linker between the PEG chains and the conjugating arm, while Mal-ethyl-PEG reagent has an ethyl linker. Thus in the former case, a longer linker chain is used and the presence of phenyl group in the linker, makes the chain rigid in this part of the anchoring where as the absence of the phenyl ring in the latter case gives the PEG chains attached to Hb gives a higher degree of rotational freedom. On the other hand, the Enzon PEG-Hb does not have an activation arm, and hence the PEG-chain is closer to the protein surface. It has an acetamidyl moiety as the conjugating group, and no linker group between the conjugating unit and the PEG-chains. Since the isopeptide linkage of the conjugating arm is expected to have a partial double bond character, one can also anticipate a degree of rigidity intrinsic to this chemical approach of PEGylation. Thus, in the Enzon stategy (conservative PEGylation approach), places the PEG very close to the protein surface (within 2 to 3 Å from the original positive charge of the $\epsilon$-amino group) while the thiolation mediated PEG maleimide based PEGylation places the PEG-chain at a distance from the protein surface (about 15 to 21 Å away in the extended conformation from the original positive charge of the $\epsilon$-amino groups). Therefore, the PEG-shell generated conservative PEGylation could have a well defined hydration sphere of Hb between the protein core and the PEG-shell. This suggests that the molecular density of the PEG within the PEG-shell of PEGylated Hb is a function of both linker chemistry (linkage between PEG and maleimide) and the coupling chemistry, the linage between PEG and Hb side chains.

The important finding of the present invention is that $(PEG_{5K})_6$-Hb is non-hypertensive. What are the physical/chemical properties of $(PEG_{5K})_6$-Hb that resulted in the neutralization of the intrinsic hypertensive activity of acellular Hb. $(PEG_{5K})_6$-HbA is certainly a size enhanced Hb molecule. Enhancing the molecular size of Hb has been one of the early design strategies advanced to overcome the hypertensive activity of Hb based on a concept that Hb extravasates into the interstitial space and would therefore be a more effective in trapping the NO than the Hb circulating in the plasma. This concept seems to be supported by the observation that oligomerized Hb with the molecular size in the range of 250 KDa are less vasoactive. It is of interest to note here that more recently Matheson et.al. have produced an oligomerized product that has a molecular size far in excess of 300 kDa and with an average molecular radius of 24 nm (a heterogeneous product with the radii distributed between 12 and 33 nm) does not appear in the renal hilar lymph indicating the absence of extravasation. This product also completely inhibited the pressor response. The observation by Sakai demonstrates a correlation with the molecular size and pressor effets, the extent of pressor response is inversely proportional to the molecular size. Encapsulated Hb with diameters near 1000 nm do not produce vasoconstriction. However, the molecular size of $(PEG_{5K})_6$-Hb is only around 7 nm and is comparable to the molecular size of the present version of many oligomerized Hb that are in clinical trails. Since most of these exhibit varying degrees of vasocontriction., the size enhancement by itself could not be primary factor that made $(PEG_{5K})_6$-Hb non-hypertensive.

However, the fact that the conservatively PEGylated Hb of the present invention carries, on an average, six copies of PEG-5000 chains is non-hypertensive and exhibits viscosity and oncotic pressure close to that of Enzon PEG-Hb exposes some potential advantages of the new conservative PEGylation technology of the present invention. (i) Conservative PEGylation of Hb with six copies of PEG-5000 chains per tetramer gives a size enhancement (increase in the hydrodynamic volume) better than that given by the non-conservative PEGylation of bovine Hb with ten copies of PEG-5000 chains. (ii) The higher efficiency to increase the hydrodynamic volume on conservative PEGylation suggest that the packing of the PEG-chains on molecular surface of Hb is less dense. This is consistent with the calculated molecular density of PEG in the new hydrated shell (water filled envelop) generated by PEG-chains around the Hb molecule. (iii) Conservative PEGylation Technology increases the viscosity and oncotic pressure more efficiently than the than the non-conservatively PEGylation; this becomes when the comparison is normalized on a PEG-5000 chain covalently attached to Hb. This suggests the potential role of molecular density of PEG in the new PEG shell generated around Hb by PEGylation in determining the viscosity changes associated with the surface decoration with PEG, and their propensity to generate a non-hypertensive Hb molecule.

The early designs of Hb based oxygen carriers had attempted to mimic the oxygen affinity of erythrocytes, to have a low oxygen affinity. The choice of Bovine Hb to generated PEGylated Hb by Enzon was to endow the final product with a low oxygen affinity. Though the oxygen affinity of bovine Hb increased on nonconservative PEGylation, the oxygen affinity of the present conservatively PEGylated Hb is considerably higher than that of Enzon Pegylated Hb. The autoregulatory theory has revealed that when infused with Hb based oxygen carries of low oxygen vasoconstriction occurs as a consequence of over supply of oxygen in the arterial side of the circulation. It predicts, that vasoconstriction can be reduced by increasing the oxygen affinity of the Hb based oxygen carrier. The oxygen affinity of $(PEG_{5K})_6$-HbA is higher than Enzon PEG-Hb, and the non-hypertensive aspect of present conservatively PEGylated Hb with only six copies PEG-5000 chains (as compared to that of ten copies of PEG-5000 in the Enzon PEG-Hb that has a slightly lower oxygen affinity than the present conservatively PEGylated Hb) may be reflection of the contribution of the higher oxygen affinity of the present preparation. accordingly, we speculate that the non-hypertenisve property of $(PEG_{5K})_6$-Hb is a multi factorial event, and requires the design of multiple species of Hb, that mimics only one of the physical or functional properties of Hb and establishing the vasoactivity of these molecules.

$(PEG_{5K})_6$-Hb, the conservatively PEGylated Hb has many of the attributes that have been advanced over the years needed to minimizing the vasoactivity of acellular Hb: (i) increased oxygen affinity of Hb to limit the oxygen off-loading by acellular Hb in vasoactive arterioles; (ii) retention of the cooperative binding to insure off loading of oxygen in the capillary beds; (iii) an enhanced molecular size (hydrodynamic volume) to reduce the extravazation; (iv) an increase in the viscosity of Hb solution both to create appropriate shear stress on the arteriole walls and to lower the diffusion constants for oxy Hb and of oxygen, carbon dioxide and/or nitric oxide; and (v) an increased colloidal pressure than the conventional modified Hbs, which increases the effectiveness of the blood substitute as a plasma expander which is feature designed in the formulation of many plasma expanders. Thus the observation that $(PEG_{5K})_6$-Hb does not come as a surprise.

Though the identity(ies) of the various physical parameters and functional properties endowed to $(PEG_{5K})_6$-Hb that makes this molecule in not clear at this stage, this new conservatively PEGylated Hb should be considered as a member of new of a new class of Hb based oxygen carriers that departs away from the conventional design strategies of developing Hb based oxygen carriers. It also should be noted here, that endowing a set of colligative properties and oxygen affinity by itself is not sufficient to make the Hb molecule non-hypertensive. As shown recently by Manjula et al (2003) increasing the molecular volume of a high oxygen affinity (the oxygen affinity comparable to that of $(PEG_{5K})_6$-Hb] PEGylated Hb [site specifically PEGylated at Cys-93($\beta$)], the viscosity and the oncotic pressure increased but without any significant changes in the vasoactivity of Hb. On the other hand, $(PEG_{5K})_6$-Hb that has a lower net mass of PEG-chain per tetramer than the $(PEG_{20})_2$-Hb is non-hypertensive. The better shielding of the molecular surface of Hb by six copies of PEG-5K chains relative to that afforded by two copies of PEG-20K is probably the best explanation for this observation. This raises an important question as to whether the positioning of the PEG-5K chains on the molecular surface of Hb plays any role in achieving the shielding of the molecular surface of Hb, if so this may be what is contributed by the iminothiolane mediated thiolation of Hb. Identification of the sites of Hb thiolated by iminothiolane and preparation of site specifically PEGylated Hb with well defined number copies of PEG-5000 chains is critical to gain insight into this aspect of the PEGylation reaction. Since the Enzon PEGylated Hb, first example of non-hypertensive Hb belong to the class of PEGylated carries ten PEG-chains, it is also not clear whether a higher level of PEGylation of Hb is needed to generate a non-hypertensive Hb when non-conservative protocol is used for generating PEGylated Hb and also as to what is the optimal level of PEGylation, oxygen affinity that is needed to generate a non-hypertensive Hb.

The iminothiolane dependent thiolation mediated, PEG-maleimide based surface decoration of the molecule with PEG-5000 chains has overcome the present major impediment in the development of Hb based oxygen carriers, namely the hypertensive activity of acellular Hb. The PEGylation technology developed here, is very simple, can be carried out under oxy conditions and does not involve cumbersome chromatographic purification protocols to isolate the PEGylated Hb. In the design, this Conservative PEGylation Technology, special considerations were given for minimizing the side reactions, particularly in comparison to the acylation reaction, the non-conservative PEGylation reaction used to develop Enzon PEGylated Hb. The selectivity of amidination of the $\epsilon$-amino groups of Hb by iminothiolane, high efficiency of the derivatization that is considerably higher than the acylation of the $\alpha$ and the $\epsilon$-amino groups either using active esters or anhydrides are some of the, advantageous aspects of this new PEGylation Protocol. The stability of iminothiolane as well as PEG-maleimide is considerably higher than the succinimidyl active esters and the acid anhydrides of PEG-acids. Accordingly, the excess of PEG-maleimide needed to introduce a given number of PEG-chains by the iminothiolane mediated conservative thiolation will be considerably lower than that will be needed in the non-conservative PEGylation protocol used to generate the earlier version of the non-hypertensive PEGylated Hb. Production of non-hypertensive Hb molecule by this technology does not need a complex deoxygenation set ups. Accordingly, the new PEGylation Technology is very cost effective for generating a non-hypertensive Hb.

Macdonald, V. W. and Motterlini. R. (1994) Vasoconstrictor effects in isolated rabbit heart perfused with bis(3,5-dibromosalicyl) fumarate crosslinked hemoglobin. *Artificial Cells, Blood Substitutes and Immobilization Biotechnology* 22:565-575.

TABLE I

Molecular Dimensions of HbA PEGylated with Mal-Phe-PEG

| Sample | Mass daltons | Radius nm | Molecular Volume nm$^3$ | PEG Mass daltons | Increase in volume | PEG Mass/Inc. in Vol (Molecular density in the PEG shell) |
|---|---|---|---|---|---|---|
| HbA | 64000 | 3.12 | 127 | 0 | — | — |
| P5K2-HbA | 74000 | 4.2 | 310 | 10000 | 183 | 54.6 |
| P10K2-HbA | 84000 | 5.54 | 712 | 20000 | 585 | 34.2 |
| P20K2-HbA | 104000 | 7.0 | 1436 | 40000 | 1309 | 30.6 |
| P5K6-HbA | 94000 | 6.81 | 1322 | 30000 | 1195 | 25.1 |
| P10K6-HbA | 124000 | 9.25 | 3314 | 60000 | 3186 | 18.8 |
| Enzon PEG-Hb (P5K10-Bovine Hb) | 114000 | 5.53 | 708 | 50000 | 581 | 86.1 |
| Octamer | 128000 | 4.12 | 293 | — | — | — |
| Dodecamer | 192000 | 5.56 | 720 | — | — | — |

TABLE II

Oxygen affinity of (PEG$_{5K}$)$_6$-HbA and its Modulation by Allosteric Effectors

| Buffer | HbA | (PEG$_{5K}$)$_6$-HbA |
|---|---|---|
| Without effectors | 8.0 (2.5) | 6.5 (2.2) |
| DPG | 22.5 (2.3) | 5.5 (2.0) |
| NaCl | 24.0 (2.4) | 8.2 (1.9) |
| L35 | 57.0 (1.7) | 12.0 (1.5) |
| PBS | 15.3 (2.7) | 8.5 (1.8) |

The oxygen affinity of the samples were determined in 50 mM Bis-tris/50 mM tris acetate, pH 7.4 and at 37° C. using Hem-O-scan. The protein concentration was maintained around 0.6 mM. The samples analyzed had less than 2% met Hb.

LIST OF CITED REFERENCES

Savitsky J, Doczi J, Black J et al. A clinical safety trial of stroma-free hemoglobin. Clin Pharmacol Therap 1978;23: 73-80.

Sloan E P, Koenigsberg M, Gens D et al. Diaspirin cross-linked hemoglobin (DCLHb) in the treatment of severe traumatic hemorrhagic shock. A randomized controlled efficacy trial. J Amer Med Assoc 1999;282:1857-64.

Saxena R, Wijnhoud A D, Carton H et al. Controlled safety study of a hemoglobin-based oxygen carrier, DCLHb, in acute ischemic stroke. Stroke 1999;30:993-6.

Hess, J. R., Macdonald, V. W. and Brinkley, W. W. (1993) Systemic and pulmonary hypertension after resuscitation with cell free hemoglobin. *J.Appl.Physiol.* 74:1769-1778.

Thomson, A., McGarry, A. E., Valeri, C. R. and Lieberthal. W. (1994) Stroma-free hemoglobin increases blood pressure and GFR in the hypotensive rat: role of nitric oxide. *J.Appl. Physiol.* 77:2348-2354.

Muldoon, S. M., Ledvina, M. A., Hart, J. L. and Macdonald, V. W. (1996) Hemoglobin-induced contraction of pig pulmonary veins. *J.Lab.Clin.Med.* 128:579-584.

Furchgott, R. (1984) The role of endothelium in the responses of vascular smooth muscle to drugs. Ann. Rev. Pharmacol. 24:175-197.

Kilbourn, R., Ghislaine, J., Cashon, B., DeAngelo, J. and Bonaventura. J. (1994) Cell-free hemoglobin reverses the endotoxin mediated hyporesponsivity of rat aortic rings to a-adrenergic agents. *Biochem. Biophys. Res. Commun.* 199: 155-162.

Doherty D H, Doyle M P, Curry S R et al. Rate of reaction with nitric oxide determines the hypertensive effect of cell-free hemoglobin. Nature Biotechnology 1998;16:672-6.

Winslow, R. M., Gonzales, A., Gonzales, M. L., Magde, M. D., McCarthy, M., Rohlfs, R. J. and Vandegriff. K. D. (1998) Vascular resistance and efficacy of red cell substitutes in a rat hemorrhage model. *J.Appl.Physiol.* 85:993-1003.

Vandegriff, K. D., Rohlfs, R. J. and Winslow, R. M. (1997) Colloid osmotic effects of hemoglobin-based oxygen carriers. In Advances in Blood Substitutes: Industrial Opportunities and Medical Challenges. R. M. Winslow, K. D. Vandegriff, and M. Intaglietta, editors. Birkhauser, Boston. 207-227.

Vandegriff K, McCarthy M, Rohlfs R et al. (1998) Colloid osmotic properties of modified hemoglobins: chemically cross-linked versus polyethylene glycol surface-conjugated. Biophys Chem 1997;69:23-30.

Winslow R M, Vandegriff K D. Hemoglobin oxygen affinity and the design of red cell substitutes. In: Winslow R M, Vandegriff K D, Intaglietta M, eds. Advances in Blood Substitutes. Industrial Opportunities and Medical Challenges. Boston: Birkhäuser, 1997;167-88.

Vandegriff K, Winslow R. A theoretical analysis of oxygen transport: A new strategy for the design of hemoglobin-based red cell substitutes. In: Winslow R, Vandegriff K, Intaglietta M, eds. Blood substitutes. Physiological basis of efficacy. New York: Birkhäuser, 1995;143-54.

McCarthy M R, Vandegriff K D, Winslow R M. The role of facilitated diffusion in oxygen transport by cell-free hemoglobin: Implications for the design of hemoglobin-based oxygen carriers. Biophysical Chemistry 2001;92:103-17.

Acharya, A. S., Manjula, B. N. and Smith, P. K. Hemoglobin crosslinkers. (1996) U.S. Pat. No. 5,585,484.

Winslow R M. New transfusion strategies: Red cell substitutes. Ann Rev Med 1999;50:337-53.

Traut, R. R., Bollen, A., Sun, T. T., Hershey, J. W. B., Sundberg, J., and Pierce, L. R., (1973). Methyl mercapto bytyrimidate as a cleavable croo-linking reagent and its application to the *Escherichia coli* 30 S ribosome, Biochemistry, 12, 3266.

Acharya A. S. and Manning J. M. (1983) Reaction of glycolaldehyde with proteins: Latent crosslinking potential of α-hydroxy aldehydes. *Proc.Natl.Acad.Sci., U.S.A.* 80:3590-3594.

Ampulski R, Ayers V, Morell S. Determination of the Reactive Sulfhydryl Groups in Heme Proteins with 4,4'-dipyridinedisulfide. Biochem Biophys Acta 1969;163-9.

Juszczak, L. J., Manjula B. N., Bonaventura, C., Acharya A. S. and Friedman, J. M. (2002) UV Resonance Raman study of β93-modified hemoglobin A: Chemical modifier-specific effects and added influences of attached poly(ethylene glycol) chains. *Biochemistry* 41:376-385.

Khan, I, Dansker, D., Samuni, U., Friedman, A. J., Bonaventura, C., Manjula B. N., Acharya, A. S. and Friedman, J. M. (2001) Cys-93(b) modified hemoglobin: Kinetic and conformational consequences. *Biochemistry* 40:7581-7592.

Mirhashemi et al., (1998) Effects of hemodilution on skin microcirculation. *Am J. Physiol. (Heart Circ. Physiol.* 23) 254:H411-H416.

Tsai et al. (1996) Microvascular oxygen distribution: effects due to free hemoglobin plasma. In Blood Substitutes. New Challenges. R. M. Winslow, K. D., Vandegriff and M. Intaglietta, editors, Boston. 124-131.

Matheson, et al. (2002). Vascular response to infusions of a nonextravasating hemoglobin polymer. *J. Appl. Physiol.* 93: 1479-86.

Sakai et al. (2000). Molecular dimensions of Hb-based O2 carriers determine constriction of resistance arteries and hypertension. *Am. J. Physiol.* 279:H908-H915.

All publications mentioned herein above, whether to issued patents, pending applications, published articles, or otherwise, are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A process for preparing a hemoglobin molecule (Hb) modified to have on average six ± one polyethylene glycol (PEG) chains, comprising the steps of:
    (a) reacting Hb with 8-15 fold molar excess of iminothiolane to form thiolated Hb; and
    (b) reacting the thiolated Hb with 16-30 fold molar excess of PEG functionalized with a maleimide moiety, to form the modified Hb having on average six ± one PEG chains.

2. The process of claim 1, wherein Hb is reacted with 9-12 fold molar excess iminothiolane in step (a).

3. The process of claim 1, wherein Hb is reacted with about 10 fold molar excess iminothiolane in step (a).

4. The process of claim 1, wherein the thiolated Hb is reacted with 18-22 fold molar excess PEG functionalized with a maleimide moiety in step (b).

5. The process of claim 1, wherein the thiolated Hb is reacted with about 20 fold molar excess PEG functionalized with a maleimide moiety in step (b).

6. The process of claim 1, wherein Hb is reacted with 9-12 fold molar excess iminothiolane in step (a), and the thiolated Hb is reacted with 18-22 fold molar excess PEG functionalized with a maleimide moiety in step (b).

7. The process of claim 1, wherein Hb is reacted with 9-12 fold molar excess iminothiolane in step (a), and the thiolated Hb is reacted with about 20 fold molar excess PEG functionalized with a maleimide moiety in step (b).

8. The process of claim 1, wherein Hb is reacted with about 10 fold molar excess iminothiolane in step (a), and the thiolated Hb is reacted with 18-22 fold molar excess PEG functionalized with a maleimide moiety in step (b).

9. The process of claim 1, wherein Hb is reacted with about 10 fold molar excess iminothiolane in step (a), and the thiolated Hb is reacted with about 20 fold molar excess PEG functionalized with a maleimide moiety in step (b).

10. The process of claim 1, wherein PEG has a molecular weight of 3000-10,000 daltons.

11. The process of claim 10, wherein the modified Hb does not produce hypertension in a subject.

12. The process of claim 1, wherein PEG has a molecular weight of about 5,000 daltons.

13. The process of claim 12, wherein the modified Hb does not produce hypertension in a subject.

14. The process of claim 1, wherein the modified Hb does not produce hypertension in a subject.

\* \* \* \* \*